United States Patent
Hayashida et al.

(10) Patent No.: US 11,712,286 B2
(45) Date of Patent: Aug. 1, 2023

(54) TREATMENT SYSTEM, CONTROL DEVICE AND TREATMENT METHOD

(71) Applicant: OLYMPUS CORPORATION, Hachioji (JP)

(72) Inventors: Tsuyoshi Hayashida, Hachioji (JP); Satomi Sakao, Hachioji (JP); Tatsuro Yamamoto, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 1052 days.

(21) Appl. No.: 16/170,616

(22) Filed: Oct. 25, 2018

(65) Prior Publication Data

US 2019/0059990 A1    Feb. 28, 2019

Related U.S. Application Data

(63) Continuation of application No. PCT/JP2016/063095, filed on Apr. 26, 2016.

(51) Int. Cl.
*A61B 18/14* (2006.01)
*A61B 17/32* (2006.01)
(Continued)

(52) U.S. Cl.
CPC .. *A61B 18/1445* (2013.01); *A61B 17/320092* (2013.01); *A61B 5/02233* (2013.01);
(Continued)

(58) Field of Classification Search
CPC ........ A61B 18/1445; A61B 17/320092; A61B 2018/00589; A61B 2090/064; A61B 5/02233
See application file for complete search history.

(56) References Cited

U.S. PATENT DOCUMENTS

2007/0066969 A1*  3/2007  McGreevy ......... A61B 18/1442
                                                     606/51
2010/0042101 A1*  2/2010  Inagaki ............. A61B 18/1442
                                                     606/52
(Continued)

FOREIGN PATENT DOCUMENTS

JP    2011-504794 A    2/2011
JP    2011-206554 A    10/2011
(Continued)

OTHER PUBLICATIONS

Jun. 20, 2017 Office Action issued in Japanese Patent Application No. 2017-522209.
(Continued)

*Primary Examiner* — Joanne M Rodden
*Assistant Examiner* — Abigail M Ziegler
(74) *Attorney, Agent, or Firm* — Oliff PLC

(57) ABSTRACT

In a treatment system, an energy treatment instrument includes a pair of grasping pieces. An energy output source outputs electric energy to the energy treatment instrument, thereby applying treatment energy to a blood vessel grasped between the grasping pieces. A measurement section measures a blood pressure at a site related to the grasped blood vessel. A processor controls output of the electric energy from the energy output source based on a measurement result obtained by the measurement section, and thereby switches an actuation state of the energy treatment instrument between a first mode for coagulating the blood vessel and a second mode for coagulating the blood vessel target that is different from the first mode.

21 Claims, 11 Drawing Sheets

(51) Int. Cl.
*A61B 17/00* (2006.01)
*A61B 90/00* (2016.01)
*A61B 18/00* (2006.01)
*A61B 5/022* (2006.01)

(52) U.S. Cl.
CPC ............... *A61B 2017/00026* (2013.01); *A61B 2017/320094* (2017.08); *A61B 2017/320095* (2017.08); *A61B 2018/00041* (2013.01); *A61B 2018/0063* (2013.01); *A61B 2018/00404* (2013.01); *A61B 2018/00589* (2013.01); *A61B 2018/00702* (2013.01); *A61B 2018/00761* (2013.01); *A61B 2018/00827* (2013.01); *A61B 2018/00875* (2013.01); *A61B 2018/00892* (2013.01); *A61B 2018/00994* (2013.01); *A61B 2090/034* (2016.02); *A61B 2090/064* (2016.02); *A61B 2090/065* (2016.02)

(56) References Cited

U.S. PATENT DOCUMENTS

| | | | | |
|---|---|---|---|---|
| 2011/0118736 | A1* | 5/2011 | Harper | A61B 5/1076 606/51 |
| 2012/0022526 | A1* | 1/2012 | Aldridge | A61B 18/1445 606/45 |
| 2012/0143182 | A1* | 6/2012 | Ullrich | A61B 18/1445 606/49 |
| 2012/0226272 | A1* | 9/2012 | Chernov | A61B 5/0295 606/34 |
| 2015/0018816 | A1* | 1/2015 | Latimer | A61B 18/1445 606/41 |
| 2016/0270841 | A1* | 9/2016 | Strobl | A61B 18/1233 |
| 2017/0238991 | A1* | 8/2017 | Worrell | H05K 3/0011 |

FOREIGN PATENT DOCUMENTS

| | | |
|---|---|---|
| JP | 2014-195648 A | 10/2014 |
| JP | 2015-93 A | 1/2015 |
| WO | 2011/052349 A1 | 5/2011 |
| WO | 2012/061638 A1 | 5/2012 |

OTHER PUBLICATIONS

May 31, 2016 International Search Report issued in Patent Application No. PCT/2016/063095.

Oct. 30, 2018 International Preliminary Report on Patentability issued in International Patent Application No. PCT/JP2016/063095.

* cited by examiner

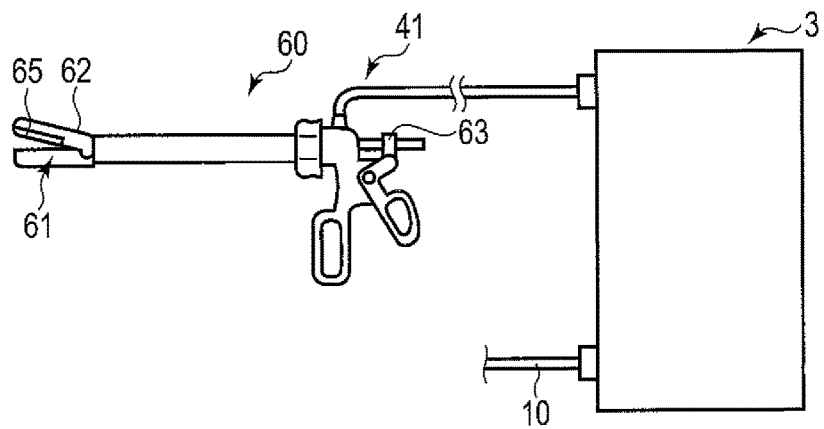
F I G. 3
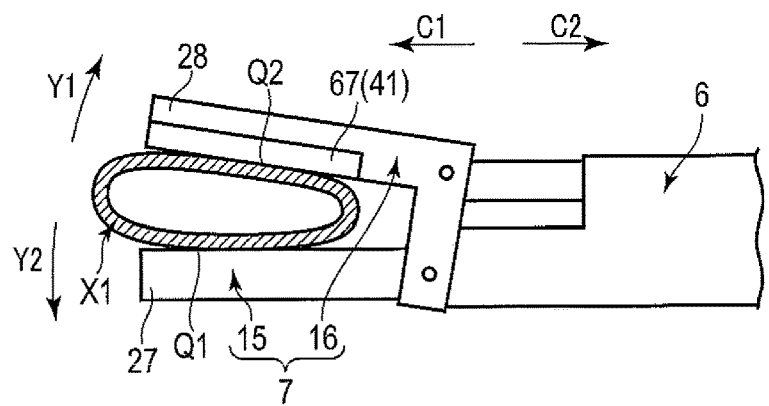
F I G. 4
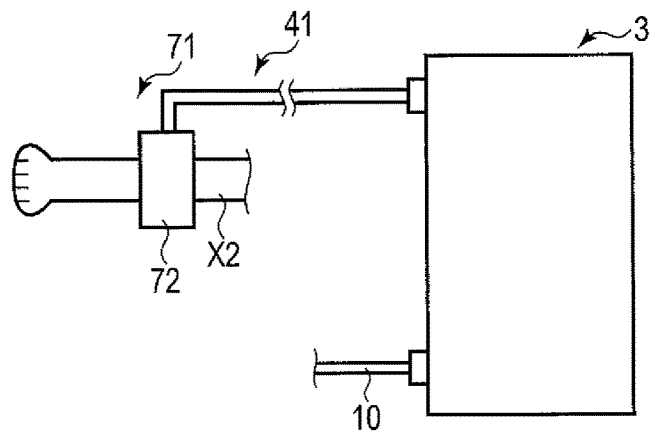
F I G. 5

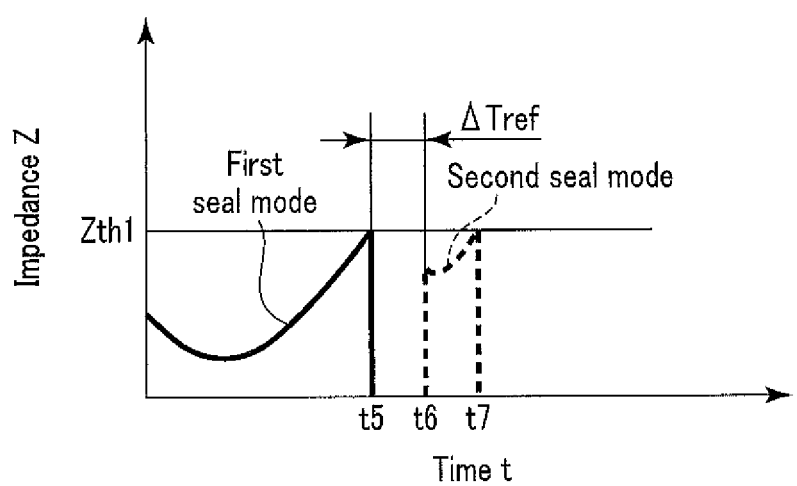
F I G. 11

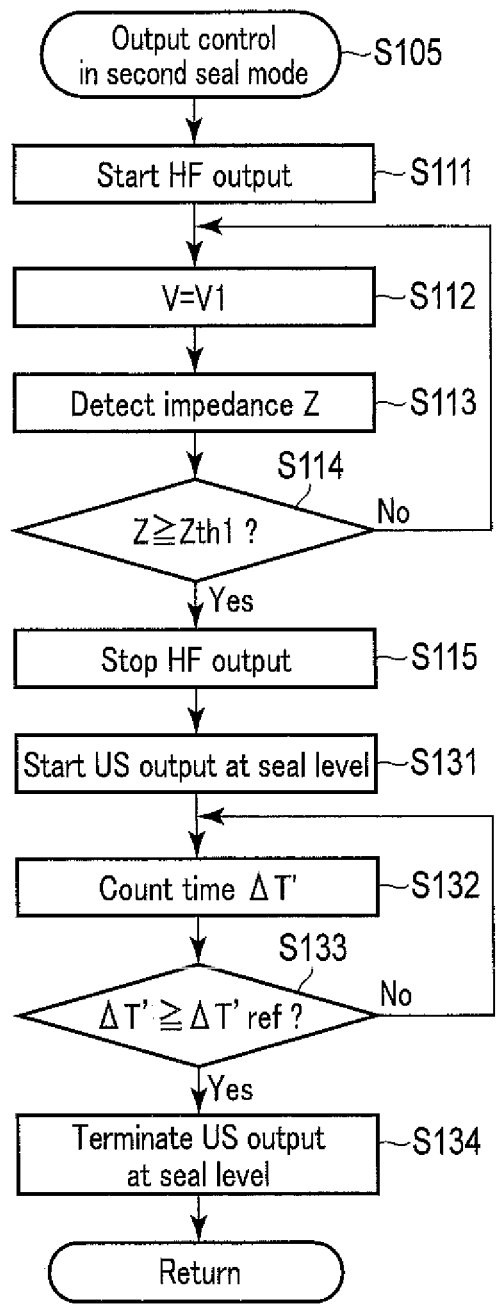
F I G. 12

US 11,712,286 B2

TREATMENT SYSTEM, CONTROL DEVICE AND TREATMENT METHOD

This is a Continuation Application of PCT Application No. PCT/JP2016/063095, filed Apr. 26, 2016, the entire contents of which are incorporated herein by reference.

BACKGROUND

Exemplary embodiments relate to a treatment system including an energy treatment instrument which applies treatment energy to a treatment target grasped between a pair of grasping pieces, and relates to a control device used with the energy treatment instrument and treatment method.

PCT International Publication No. 2012/061638 discloses an energy treatment instrument which grasps a treatment target, such as a biological tissue, between a pair of grasping pieces. In this energy treatment instrument, the grasping pieces are respectively provided with electrodes. When electric energy is supplied to both electrodes, a high-frequency current flows between the electrodes through the grasped treatment target. The high-frequency current is thereby applied as treatment energy to the treatment target.

SUMMARY

According to at least one exemplary embodiment, a treatment system includes an energy treatment instrument including a first grasping piece, and a second grasping piece configured to grasp a blood vessel between the first grasping piece and the second grasping piece; an energy output source configured to output electric energy to be supplied to the energy treatment instrument, and configured to supply the electric energy to the energy treatment instrument so that treatment energy is applied to the blood vessel grasped between the first grasping piece and the second grasping piece; a measurement section configured to measure a blood pressure at a site related to the grasped blood vessel; and a processor configured to control output of the electric energy from the energy output source, based on a measurement result obtained by the measurement section, and thereby configured to switch an actuation state of the energy treatment instrument between a first mode for coagulating the blood vessel and a second mode for coagulating the blood vessel, the second mode being different from the first mode.

According to another exemplary embodiment, a control device is used with an energy treatment instrument, the energy treatment instrument including a first grasping piece, and a second grasping piece configured to open and close with respect to the first grasping piece so as to grasp a blood vessel between the first grasping piece and the second grasping piece, the control device including: an energy output source configured to output electric energy that is to be supplied to the energy treatment instrument, and configured to supply the electric energy to the energy treatment instrument so that the treatment energy is applied to the blood vessel grasped between the first grasping piece and the second grasping piece; and a processor configured to obtain a blood pressure at a site related to the grasped blood vessel, the processor being further configured to perform at least one of controlling output of the electric energy from the energy output source based on the obtained blood pressure, and increasing a grasping force of the blood vessel between the first grasping piece and the second grasping piece when the obtained blood pressure is greater than or equal to a threshold in comparison to when the blood pressure is lower than the threshold.

According to another exemplary embodiment, a treatment method includes that: grasping a treatment target between a first grasping piece and a second grasping piece by using an energy treatment instrument, the energy treatment instrument including the first grasping piece, and the second grasping piece configured to open and close with respect to the first grasping piece; outputting electric energy that is to be supplied to the energy treatment instrument so that treatment energy is applied to the treatment target grasped between the first grasping piece and the second grasping piece; measuring a blood pressure at a site related to the grasped blood vessel; and controlling output of the electric energy based on a measurement result of the blood pressure, and thereby switching an actuation state of the energy treatment instrument between a first mode for coagulating the blood vessel and a second mode for coagulating the blood vessel, the second mode being different from the first mode.

Advantages will be set forth in the description which follows, and in part will be apparent from the description, or may be learned by practice of exemplary embodiments. The advantages may be realized and obtained by means of the instrumentalities and combinations particularly pointed out hereinafter.

BRIEF DESCRIPTION OF THE DRAWINGS

The accompanying drawings, which are incorporated in and constitute a part of the specification, illustrate exemplary embodiments.

FIG. 3 is a schematic diagram showing a measurement section according to an example of an exemplary embodiment;

FIG. 4 is a schematic diagram showing a measurement section according to another example of an exemplary embodiment;

FIG. 5 is a schematic diagram showing a measurement section according to yet another example of an exemplary embodiment;

FIG. 11 is a schematic diagram illustrating an example of a variation with time of an impedance between the pair of grasping pieces, in a state in which the processor according to an exemplary embodiment is executing the output control in the first seal mode and in the second seal mode;

FIG. 12 is a flowchart illustrating a process executed in the second seal mode of the output control by the processor according to an exemplary embodiment;

DETAILED DESCRIPTION

Figure 1:
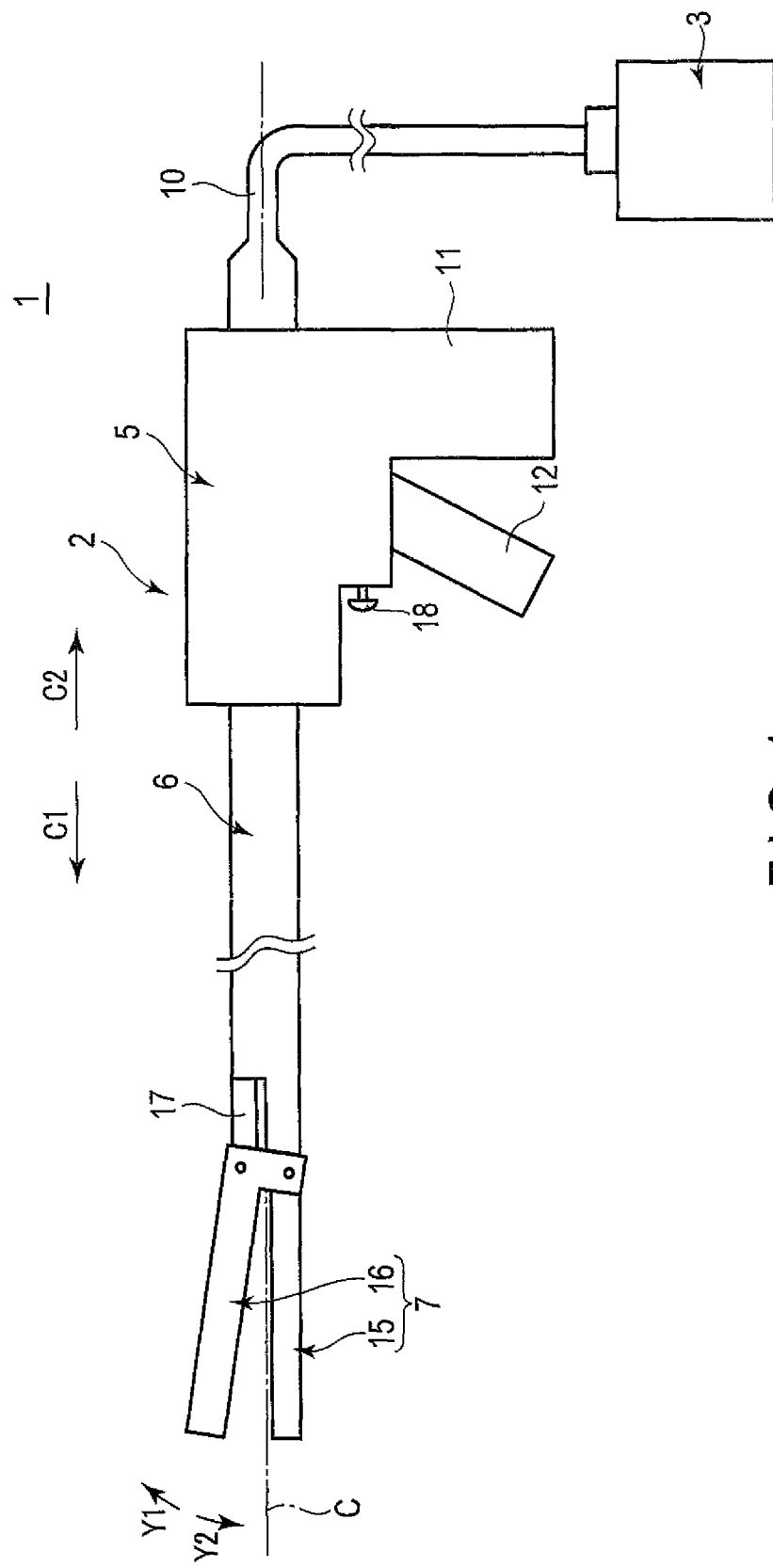
FIG. 1 is a schematic diagram illustrating a treatment system according to an exemplary embodiment.

An exemplary embodiment will be described with reference to FIGS. 1 to 8. FIG. 1 is a view illustrating a treatment system 1 according to the present embodiment. As illustrated in FIG. 1, the treatment system 1 includes an energy treatment instrument 2 and a control device (energy control device) 3. The energy treatment instrument 2 has a longitudinal axis C. Here, one side of a direction along the longitudinal axis C is defined as a distal side (arrow C1 side), and the side opposite to the distal side is defined as a proximal side (arrow C2 side).

The energy treatment instrument 2 includes a housing 5 which can be hand-held, a sheath (shaft) 6 coupled to the distal side of the housing 5, and an end effector 7 provided on a distal portion of the sheath 6. One end of a cable 10 is connected to the housing 5 of the energy treatment instrument 2. The other end of the cable 10 is detachably connected to the control device 3. The housing 5 is provided with a grip (stationary handle) 11, and a handle (movable handle) 12 is rotatably attached to the housing 5. In accordance with the handle 12 rotating relative to the housing 5, the handle 12 opens or closes relative to the grip 11. According to the present embodiment, the handle 12 is located on the distal side with respect to the grip 11, and the handle 12 moves substantially in parallel to the longitudinal axis C in the opening or closing motion relative to the grip 11. The embodiment, however, is not limited thereto. In one example, the handle 12 may be located on the proximal side with respect to the grip 11. In another example, the handle 12 may be located on the side opposite to the grip 11 with respect to the longitudinal axis C, and a moving direction in the opening or closing motion relative to the grip 11 may intersect with the longitudinal axis C (may be substantially perpendicular to the longitudinal axis C).

The sheath 6 extends along the longitudinal axis C. The end effector 7 includes a first grasping piece 15, and a second grasping piece 16 which opens and closes relative to the first grasping piece 15. The handle 12 and the end effector 7 are coupled via a movable member 17, the movable member 17 extending inside the sheath 6 along the longitudinal axis C. By opening or closing the handle 12, which is an opening and closing operation input section, relative to the grip 11, the movable member 17 moves along the longitudinal axis C relative to the sheath 6 and housing 5, thereby opening or closing the pair of grasping pieces 15 and 16 relative to each other. When the grasping pieces 15 and 16 are closed relative to each other, the grasping pieces 15 and 16 grasp a biological tissue, such as a blood vessel, as a treatment target. The opening and closing directions (directions of arrow Y1 and arrow Y2) of the grasping pieces 15 and 16 intersect the longitudinal axis C (i.e., they are substantially perpendicular to the longitudinal axis C).

The end effector 7 will suffice as long as the paired grasping pieces 15 and 16 can open or close relative to each other in accordance with the opening or closing motion of the handle 12. In one example, one of the grasping pieces 15 and 16 is formed integrally with the sheath 6 or fixed to the sheath 6, while the other one of the grasping pieces 15 and 16 is pivotally attached to the distal portion of the sheath 6. In another example, both of the grasping pieces 15 and 16 are pivotally attached to the distal portion of the sheath 6. In yet another example, a rod member (not shown) is inserted through the sheath 6, and a portion of the rod member (probe) projecting from the sheath 6 toward the distal side forms one of the grasping pieces 15 and 16. The other one of the grasping pieces 15 and 16 is pivotally attached to the distal portion of the sheath 6. In yet another example, a rotary knob (not shown) may be attached to the housing 5. If this is the case, by turning the rotary knob around the longitudinal axis C relative to the housing 5, the sheath 6 and the end effector 7 turn together with the rotary knob around the longitudinal axis C relative to the housing 5. In this manner, the angular position of the end effector 7 around the longitudinal axis C can be adjusted.

Figure 2:
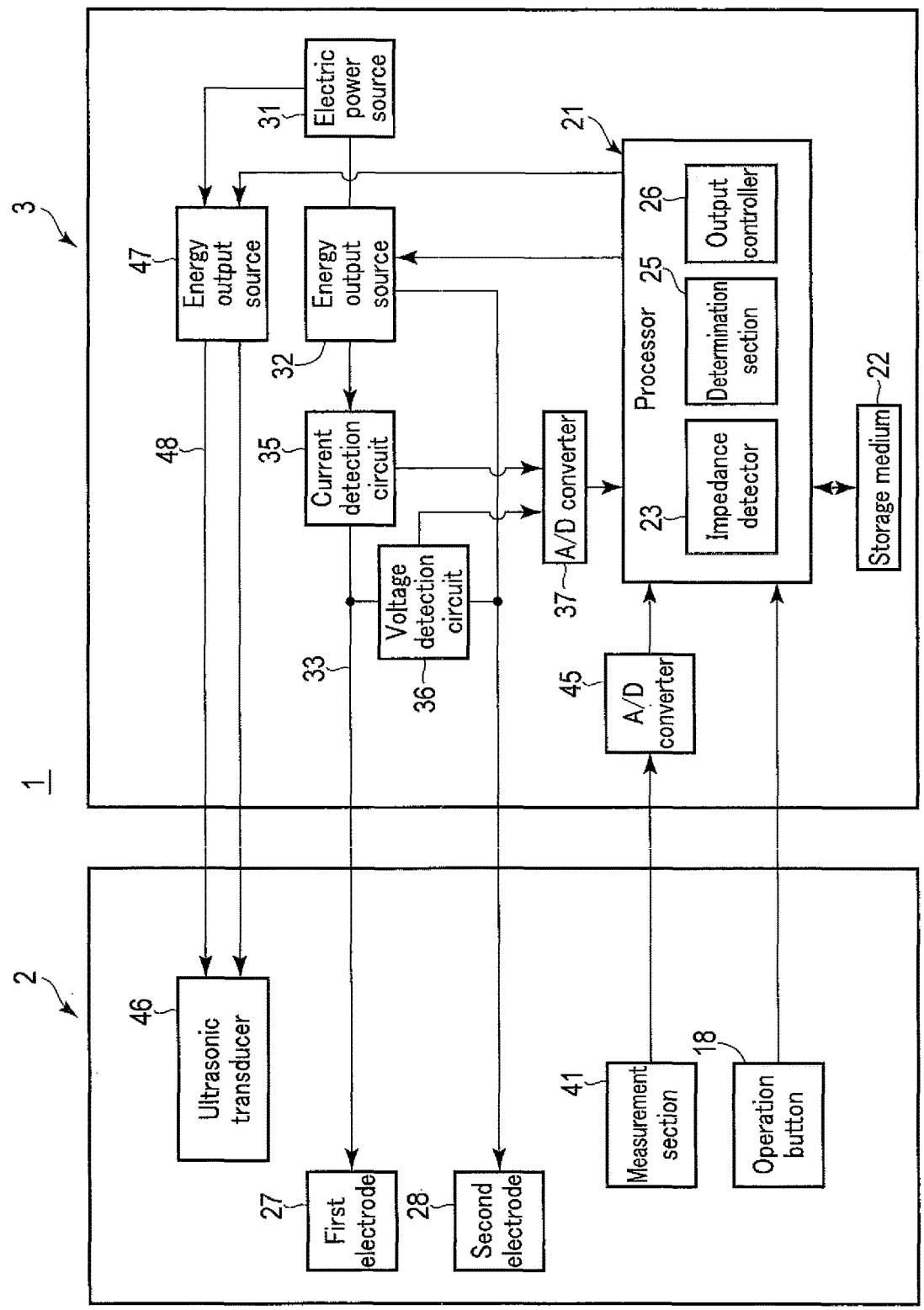
FIG. 2 is a block diagram illustrating a control configuration in the treatment system according to an exemplary embodiment.

FIG. 2 is a diagram illustrating a control configuration in the treatment system 1. As illustrated in FIG. 2, the control device 3 includes a processor (controller) 21, which controls the entire treatment system 1, and a storage medium 22. The processor 21 is formed of an integrated circuit including a Central Processing Unit (CPU), an Application Specific Integrated Circuit (ASIC), or a Field Programmable Gate Array (FPGA). The processor 21 may be formed of a single integrated circuit, or of a plurality of integrated circuits. The process in the processor 21 is executed according to a program stored in the processor 21 or storage medium 22. The storage medium 22 stores processing programs for use in the processor 21, as well as parameters and tables for use in arithmetic processes in the processor 21. The processor 21 includes an impedance detector 23, a determination section 25, and an output controller 26. The impedance detector 23, determination section 25, and output controller 26 function as parts of the processor 21, and execute some of the processes executed by the processor 21.

In the end effector 7 of the energy treatment instrument 2, the first grasping piece 15 is provided with a first electrode 27, and the second grasping piece 16 is provided with a second electrode 28. The electrodes 27 and 28 are formed of an electrically conductive material. The control device 3 includes an electric power source 31, which may be a battery or a power receptacle, and an energy output source (first energy output source) 32. The energy output source 32 is electrically connected to the electrodes 27 and 28 via an electricity supply path (first electricity supply path) 33 that extends inside the cable 10. The energy output source 32 includes a converter circuit, an amplifier circuit, and the like, and converts the electric power supplied from the electric power source 31. The energy output source 32 outputs the converted electric energy (high-frequency electric power). The electric energy that is output from the energy output source 32 is supplied to the electrodes 27 and 28 through the electricity supply path 33. The output controller 26 of the processor 21 controls the driving of the energy output source 32, and controls the output of the electric energy from the energy output source 32. In this manner, any of output electric power P, output current I and output voltage V of the energy output source 32 is adjusted, and the supply of the electric energy to the electrodes 27 and 28 is thereby controlled.

The electric energy is supplied from the energy output source 32 to the electrodes 27 and 28 with a treatment target being grasped between the grasping pieces 15 and 16. A high-frequency current thereby flows between the electrodes 27 and 28 through the grasped treatment target that is being in contact with the electrodes 27 and 28. That is, the high-frequency current is supplied as treatment energy to the treatment target. Due to the high-frequency current flowing in the treatment target, heat is caused in the treatment target, and this heat denatures the treatment target. The treatment target, such as a blood vessel, is sealed (coagulated) by using the high-frequency current. As described above, with the electric energy supplied from the energy output source 32 to the electrodes 27 and 28 of the energy treatment instrument 2, the treatment energy (high-frequency current) is applied to the treatment target grasped between the grasping pieces 15 and 16. According to the present embodiment, the grasping pieces 15 and 16 function as an energy application section (energy applier) that applies the high-frequency current as treatment energy to the grasped treatment target (blood vessel).

The electricity supply path 33 is provided with a current detection circuit 35 and a voltage detection circuit 36. When the electric energy is being output from the energy output source 32, the current detection circuit 35 detects the output current I, and the voltage detection circuit 36 detects the output voltage V. The energy control device 3 is provided with an A/D converter 37. To this A/D converter 37, an analog signal relating to the current I detected by the current detection circuit 35, and an analog signal relating to the voltage V detected by the voltage detection circuit 36 are transmitted. The A/D converter 37 converts the analog signal relating to the current I and the analog signal relating to the voltage V to digital signals, and transmits the converted digital signals to the processor 21.

When the electric energy is being output from the energy output source 32, the processor 21 acquires information relating to the output current I and the output voltage V of the energy output source 32. The impedance detector 23 of the processor 21 detects the impedance of the electricity supply path 33 including the grasped treatment target (blood vessel) and the electrodes 27 and 28, based on the output current I and the output voltage V. In this manner, an impedance Z between the paired grasping pieces 15 and 16 (i.e. the impedance of the grasped treatment target) is detected.

As illustrated in FIG. 1, an operation button 18 is attached to the housing 5 to function as an energy operation input section. By pressing the operation button 18, an operation (signal) for outputting the electric energy from the energy output source 32 to the energy treatment instrument 2 is input to the control device 3. In place of the operation button 18 or in addition to the operation button 18, a foot switch or the like may be provided separately from the energy treatment instrument 2, as the energy operation input section. As illustrated in FIG. 2, the processor 21 detects the presence or absence of input of an operation from the energy operation input section such as the operation button 18. Based on the input of the operation by the operation button 18, the output controller 26 of the processor 21 controls the output of the electric energy from the energy output source 32.

A treatment system 1 is provided with a measurement section (measurement device) 41. The measurement section 41 measures a blood pressure p at a site related to a blood vessel that is grasped between the grasping pieces 15 and 16 as a treatment target. The measurement section (detector) 41 may be arranged in the energy treatment instrument 2, or may be arranged separately from the energy treatment instrument 2. FIG. 3 illustrates an example of the measurement section 41, and FIG. 4 illustrates another example of the measurement section 41. FIG. 5 shows a yet another example of the measurement section 41.

In the example of FIG. 3, the measurement section (measurement device) 41 is provided with measurement forceps 60 separate from the energy treatment instrument 2. The measurement forceps 60 are provided with a pair of grasping pieces 61 and 62 and a damper 63. A pressure sensor 65 is provided in one of the grasping pieces 61 and 62 (e.g., grasping piece 62). The measurement forceps 60 grasps an artery between the grasping pieces 61 and 62 so that the blood pressure ρ of the grasped artery can be measured using what is called the oscillometric method.

That is, when measuring the blood pressure ρ of the artery grasped by the measurement forceps 60, the grasped artery is pressed by closing the grasping pieces 61 and 62, and the artery is thereby blocked. Thereafter, using a damper 63 or the like, the compression (blockage) of the grasped artery is gradually released, and the pressure of the artery between the grasping pieces 61 and 62 is gradually reduced. While the pressure of the grasped artery is gradually being reduced, the pressure pulse wave of the grasped artery is detected using the pressure sensor 65. Here, the blood pressure at the point where the pressure pulse wave rapidly increases is determined as a systolic blood pressure ρmax, whereas the blood pressure at the point where the pressure pulse wave rapidly drops is determined as a diastolic blood pressure ρmin. Based on the systolic blood pressure ρmax and diastolic blood pressure ρmin, the measurement section 41 detects an average blood pressure ρave of the artery between the grasping pieces 61 and 62, and thereby finds the blood pressure ρ of the artery as the average blood pressure ρave.

In the measurement of the blood pressure ρ using the measurement forceps 60, the blood pressure ρ can be measured for an artery only, and the blood pressure of a vein cannot be measured. For this reason, when an artery is grasped as a treatment target between the grasping pieces 15 and 16 of the energy treatment instrument 2 (i.e. when a sealing treatment is performed for an artery), the blood pressure ρ of the artery (treatment target) that is to be sealed is measured, and the measured blood pressure ρ is adopted as the blood pressure ρ of the site related to the blood vessel (artery) that is to be sealed. In contrast, when a vein is grasped as a treatment target between the grasping pieces 15 and 16 of the energy treatment instrument 2 (i.e. when a sealing treatment is performed for a vein), the blood pressure ρ is measured for an artery related to the to-be-sealed vein (treatment target), and the measured blood pressure ρ is adopted as the blood pressure ρ at the site related to the to-be-sealed blood vessel (vein). The blood pressure of the vein is as a level corresponding to the blood pressure of the related artery. Thus, when a vein is treated as a treatment target, the blood pressure of the treatment target vein can be determined based on the blood pressure ρ of its related artery.

In the example of FIG. 4, the measurement section 41 includes a pressure sensor 67 that is provided in one of the grasping pieces 15 and 16 (e.g., grasping piece 16) in the energy treatment instrument 2. In this example, an artery X1 is grasped between the grasping pieces 15 and 16 so that the blood pressure $\rho$ of the grasped artery X1 can be measured by what is called tonometry. In particular, when the blood pressure $\rho$ of the artery X1 between the grasping pieces 15 and 16 is to be measured, the grasping pieces 15 and 16 are closed, and the artery X1 is thereby grasped in a manner so that sites Q1 and Q2 pressed by the pieces 15 and 16 (i.e., sites in contact with the grasping pieces 15 and 16) in the outer surface of the artery X1 become flatter. By bringing a flat site (e.g., Q2) in the outer surface of the grasped artery X1 into contact with the pressure sensor 67, the blood pressure $\rho$ of the grasped artery X1 is measured by using the pressure sensor 67.

Similar to the example of FIG. 3, the blood pressure $\rho$ can be measured only for an artery, while the blood pressure for a vein cannot be measured in this example. For this reason, when an artery is grasped as a treatment target between the grasping pieces 15 and 16 of the energy treatment instrument 2 (i.e. when a sealing treatment is performed for an artery), the blood pressure $\rho$ of the artery (treatment target) that is to be sealed is measured. When a vein is grasped as a treatment target between the grasping pieces 15 and 16 (i.e. when a sealing treatment is performed for a vein), the blood pressure $\rho$ of the artery related to the vein (treatment target) that is to be sealed is measured.

In this example, the energy treatment instrument 2 may be provided with a lock member (not shown) that is configured to lock the handle 12 in a state in which the sites Q1 and Q2 of the outer surface of the grasped artery X1 pressed by the grasping pieces 15 and 16 are flattened. If this is the case, the actuation of the lock member is controlled by the processor 21. The processor 21 releases the state of the handle 12 locked by the lock member in response to an operation input from the operation button 18 (i.e., when the operation input is switched from the OFF state to the ON state). As a result, the grasping pieces 15 and 16 are closed further from the state in which the sites Q1 and Q2 of the treatment target are being pressed and being flattened by the grasping pieces 15 and 16, and treatment energy such as a high-frequency current is applied to the treatment target.

In an example of FIG. 5, the measurement section (measurement device) 41 is provided with a blood pressure measurement device 71 that is used for a medical checkup or the like. In this example, a cuff 72 of the blood pressure measurement device 71 is wound around the upper side of one arm X2, and the blood pressure $\rho$ of the main artery is thereby measured at a position immediately after the blood is pumped from the left ventricle through the main artery valve. The measured blood pressure $\rho$ is used as the blood pressure $\rho$ of the site related to the blood vessel that is to be sealed. In the same living body, the blood pressure of each of the blood vessels correspond to the blood pressure $\rho$ of the measured main artery. For this reason, the blood pressure of the blood vessel that is a treatment target can be determined, based on the blood pressure $\rho$ at the site of the main artery immediately after the blood is pumped from the left ventricle.

In this manner, in any of the examples, the measurement section 41 measures the blood pressure $\rho$ of the site related to the blood vessel that is grasped between the grasping pieces 15 and 16 (to-be-sealed blood vessel) as a treatment target. The blood pressure of the blood vessel that is the treatment target thereby corresponds to the measured blood pressure $\rho$.

As illustrated in FIG. 2, the energy control device 3 is provided with an A/D converter 45. An analog signal indicating the blood pressure $\rho$ measured by the measurement section 41 is transmitted to the A/D converter 45. The A/D converter 45 converts the analog signal indicating the blood pressure $\rho$ to a digital signal, and transmits the converted digital signal to the processor 21. In one example, the A/D converter 45 may be arranged in the measurement section 41. If this is the case, the analog signal indicating the measurement result of the blood pressure $\rho$ is converted to a digital signal by the measurement section 41, and the converted digital signal is transmitted from the measurement section 41 to the processor 21. The determination section 25 of the processor 21 determines, based on a measurement result of the blood pressure $\rho$ obtained by the measurement section 41, whether or not the measured blood pressure $\rho$ is lower than a blood pressure threshold (threshold value) $\rho$th. In the example of FIG. 5, the blood pressure threshold $\rho$th may be 130 mmHg. The blood pressure threshold $\rho$th may be set, for example, by the surgeon, or may be stored in the storage medium 22. Based on the measurement result obtained by the measurement section 41 and the determination result regarding the blood pressure $\rho$, the output controller 26 of the processor 21 controls the output of the electric energy from the energy output source 32. In accordance with the output state of the electric energy from the energy output source 32, the actuation state of the energy treatment instrument 2 is switched between a first mode (first actuation mode) and a second mode (second actuation mode). According to the present embodiment, the state of the treatment energy (high-frequency current) applied from the energy application section (grasping pieces 15 and 16) to the grasped treatment target differs between the first mode and the second mode.

In one example, an ultrasonic transducer 46 may be provided in the energy treatment instrument 2 (inside the housing 5). If this is the case, a rod member is connected to the distal side of the ultrasonic transducer 46, and one of the grasping pieces 15 and 16 (e.g., the first grasping piece 15) is constituted by a projecting portion of this rod member that projects from the sheath 6 toward the distal side. In this example, in addition to the energy output source 32, an energy output source (second energy output source) 47 is provided in the control device 3. The energy output source 47 is electrically connected to the ultrasonic transducer 46 via an electricity supply path (second electricity supply path) 48 extending inside the cable 10. The energy output source 47 may be formed integrally with the energy output source 32, or may be formed separately from the energy output source 32.

In this example, the energy output source 47 includes a converter circuit, an amplifier circuit, and the like, and converts the electric power from the electric power source 31. Then, the energy output source 47 outputs the converted electric energy (AC electric power). The electric energy that is output from the energy output source 47 is supplied to the ultrasonic transducer 46 through the electricity supply path 48. The output controller 26 of the processor 21 controls the driving of the energy output source 47, and controls the output of the electric energy from the energy output source 47.

In the present example, the electric energy (AC electric power) that is output from the energy output source 47 is supplied to the ultrasonic transducer 46 so that ultrasonic vibrations can be generated in the ultrasonic transducer 46. The generated ultrasonic vibrations are transmitted from the proximal side toward the distal side in the rod member (vibration transmitting member) so that the rod member including one of the grasping pieces 15 and 16 (e.g., first grasping piece 15) vibrates. Due to the rod member vibrating in the state of the treatment target being grasped between the grasping pieces 15 and 16, the ultrasonic vibrations are applied as treatment energy to the treatment target. At this time, frictional heat is generated from the vibrations, and the treatment target such as the blood vessel can be incised, while being sealed (coagulated), by use of the frictional heat.

In another example, a heater (not shown) may be provided, in place of the ultrasonic transducer 46, in the end effector 7 (at least one of the grasping pieces 15 and 16). If this is the case, the electric energy (DC electric power or AC electric power) that is output from the energy output source (47) is supplied to the heater through the electricity supply path (48). Heat is thereby generated by the heater, and the treatment target such as the blood vessel can be incised, while being sealed (coagulated), by use of the heat generated by the heater. When the ultrasonic vibration and the heat of the heater are applied as treatment energy to the grasped treatment target (blood vessel), at least one of the grasping pieces 15 and 16 still functions as the energy application section (energy supplier) that applies the treatment energy to the treatment target.

Next, the function and advantageous effects of the present embodiment will be described. When a treatment is performed by using the treatment system 1, a surgeon holds the housing 5 of the energy treatment instrument 2, and inserts the end effector 7 into a body cavity such as an abdominal cavity. With the blood vessel (treatment target) being placed between the grasping pieces 15 and 16, the handle 12 is closed with respect to the grip 11 so that the grasping pieces 15 and 16 can be closed relative to each other. In this manner, the blood vessel is grasped between the grasping pieces 15 and 16. The blood pressure $\rho$ of the site related to the grasped blood vessel is measured by the measurement section 41. Thereafter, a high-frequency current may be applied as treatment energy to the blood vessel so as to conduct a sealing treatment of the grasped blood vessel. The measurement of the blood pressure $\rho$ is conducted before the operation of applying the treatment energy to the blood vessel (i.e., the operation of causing the energy output source 32 to output electric energy) is input from the operation button 18.

Figure 6:
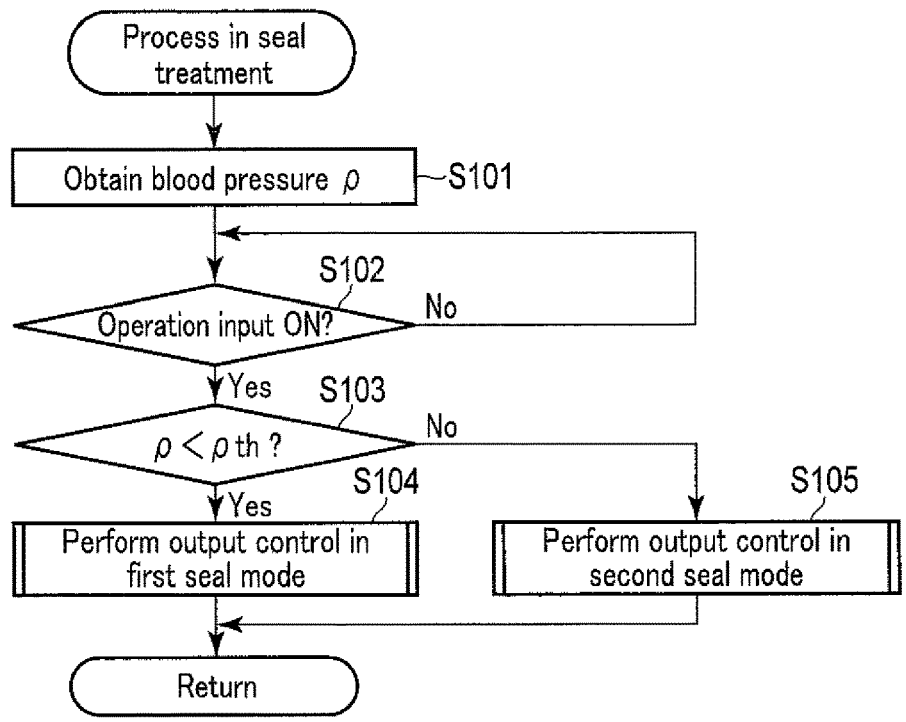
FIG. 6 is a flowchart illustrating a process executed by the processor in the seal treatment of the blood vessel using the treatment system according to an exemplary embodiment.

FIG. 6 is a flowchart illustrating the process executed by the processor 21 in the seal treatment of the blood vessel using the treatment system 1 of the present embodiment. As illustrated in FIG. 6, when performing the seal treatment of the blood vessel, the processor 21 obtains the blood pressure $\rho$ of the site related to the grasped blood vessel (step S101). That is, the measurement result achieved at the measurement section 41 is obtained.

The processor 21 determines whether an operation input has been made using the operation button (energy operation input section) 18 (i.e., whether the operation input is ON or OFF) (step S102). If no operation input is made (No at step S102), the process returns to step S102. In other words, the processor 21 is on standby until an operation input is made on the operation button 18. If an operation input is made (Yes at step S102), the determination section 25 of the processor 21 determines whether or not the obtained blood pressure $\rho$ is lower than the blood pressure threshold (threshold value) $\rho$th (step S103). That is, whether or not the blood pressure $\rho$ is greater than or equal to the blood pressure threshold $\rho$th is determined. If the blood pressure $\rho$ is lower than the blood pressure threshold $\rho$th (Yes at step S103), the output controller 26 of the processor 21 executes the output control of the electric energy from the energy output source 32 in the first seal mode (step S104). Here, the processor may determine (set) that the blood pressure of the blood vessel being grasped between the grasping pieces 15 and 16 is too low. If the blood pressure $\rho$ is greater than or equal to the blood pressure threshold $\rho$th (No at step S103), the output controller 26 executes the output control of the electric energy from the energy output source 32 in the second seal mode that is different from the first seal mode (step S105).

Figure 7:
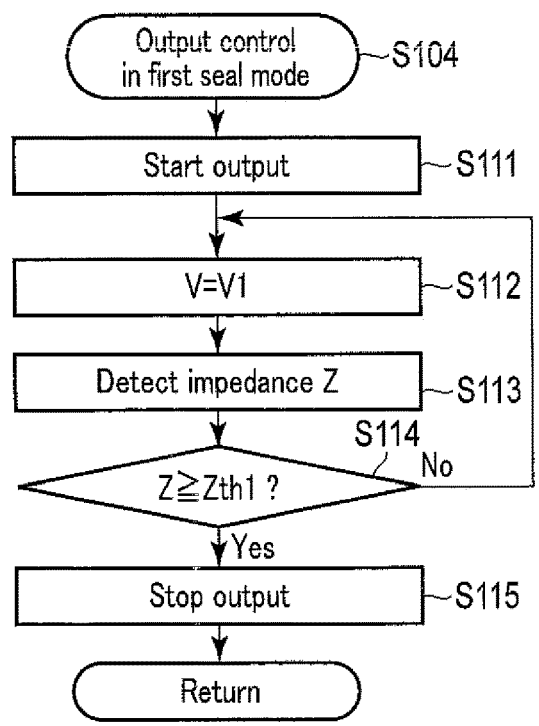
FIG. 7 is a flowchart illustrating a process executed by the processor in a first seal mode of the output control according to an exemplary embodiment.

FIG. 7 is a flowchart indicating the process of the processor 21 in the output control in the first seal mode. As illustrated in FIG. 7, the processor 21 starts the output of the electric energy (high-frequency electric power) from the energy output source (first energy output source) 32 in the first seal mode of the output control (step S111). In this manner, the electric energy is supplied to the electrodes 27 and 28, and a high-frequency current flows in the grasped blood vessel, thereby sealing the blood vessel.

If a certain period of time has elapsed from the start of the output of the electric energy from the energy output source 32, the output controller 26 executes a constant voltage control to keep the output voltage V from the energy output source 32 constant at a first voltage V1 over time (step S112). Furthermore, when the output of the electric energy from the energy output source 32 is started, the impedance detector 23 of the processor 21 detects the impedance Z between the grasping pieces 15 and 16 (i.e. the impedance of the grasped treatment target), based on the detection result of the output current I obtained by the current detection circuit 35 and the detection result of the output voltage V obtained by the voltage detection circuit 36 (step S113). Then, the processor 21 determines whether a detected impedance Z is greater than or equal to an impedance threshold (first impedance threshold) Zth1 (step S114). The impedance threshold Zth1 may be set, for example, by the surgeon, or may be stored in the storage medium 22.

If the impedance Z is lower than the impedance threshold Zth1 (No at step S114), the process returns to step S112, and the processes of step S112 and thereafter are sequentially executed. If the impedance Z is greater than or equal to the impedance threshold Zth1 (Yes at step S114), the output controller 26 stops the output of the electric energy (high-frequency electric power) from the energy output source 32 (step S115). Thus, the supply of the electric energy to the electrodes 27 and 28 is stopped. The processor 21 executes the output control of the electric energy from the energy output source 32 in the first seal mode, and thereby the energy treatment instrument 2 is actuated in the first mode in which the grasped treatment target is coagulated (the blood vessel is sealed).

In the second seal mode of the output control, the processor 21 executes the processes of steps S111 and S113 to S115, similar to the first seal mode of the output control. However, in the second seal mode, if a certain period of time has elapsed from the start of the output of the electric energy from the energy output source 32, the output controller 26 executes a constant voltage control for keeping the output voltage V from the energy output source 32 constant over time at a second voltage value V2, which is lower than the first voltage V1. Because the constant voltage control is executed at the second voltage value V2 that is lower than the first voltage V1, the electric energy that is output from the energy output source 32 is lower in the second seal mode than in the first seal mode. In other words, the output controller 26 of the processor 21 reduces the electric energy to be output from the energy output source 32 in the second seal mode, in comparison to the first seal mode. The processor 21 executes the output control of the electric energy from the energy output source 32 in the second seal mode so that the energy treatment instrument 2 coagulates the grasped treatment target (seals the blood vessel), and is actuated in the second mode which is different from the first mode. As described above, in the present embodiment, the processor 21 controls the output of the electric energy from the energy output source 32, based on the determination result of the blood pressure ρ, thereby switching the actuation state of the energy treatment instrument 2 between the first mode (first actuation mode) and the second mode (second actuation mode). The output state of the electric energy from the energy output source 32 differs between the first seal mode and the second seal mode. Thus, in the energy treatment instrument 2, the state of the treatment energy (high-frequency current) applied from the energy application section (grasping pieces 15 and 16) to the grasped treatment target differs between the first mode and the second mode.

As long as the electric energy to be output from the energy output source 32 becomes smaller in the second seal mode than in the first seal mode, the output control that is not the constant voltage control may be executed in the first seal mode and in the second seal mode. In one example, in the first seal mode, the output controller 26 may execute a constant electric power control to keep the output electric power P from the energy output source 32 constant over time at a first electric power P1. In the second seal mode, the output controller 26 executes a constant electric power control to keep the output electric power P from the energy output source 32 constant over time at a second electric power P2 that is lower than the first electric power P1. In another example, both the constant voltage control for keeping the output voltage V constant over time at the first voltage V1 and the constant electric power control for keeping the output electric power P constant over time at the first electric power P1 may be executed in the first seal mode, and switching is performed between the constant voltage control and the constant electric power control in accordance with the impedance Z. In the second seal mode, both the constant voltage control for keeping the output voltage V constant over time at the second voltage value V2 that is lower than the first voltage V1, and the constant electric power control for keeping the output electric power P constant over time at the second electric power P2 that is lower than the first electric power P1 may be executed, and switching is performed between the constant voltage control and the constant electric power control in accordance with the impedance Z. In any of the examples, the electric energy that is output from the energy output source 32 in the second seal mode is smaller than in the first seal mode.

According to the present embodiment, only the high-frequency current is applied as treatment energy to the blood vessel in each of the first seal mode and the second seal mode, and therefore the treatment energy other than the high-frequency current, such as ultrasonic vibrations and the heat of the heater, will not be applied to the blood vessel (treatment target). For instance, in the example in which the ultrasonic transducer 46 is provided in the energy treatment instrument 2, the processor 21 stops the output of the electric energy from the energy output source 47 to the ultrasonic transducer 46 in each of the first seal mode and the second seal mode. Thus, no electric energy is supplied to the ultrasonic transducer 46 in the first seal mode and second seal mode, and therefore no ultrasonic vibration will be generated by the ultrasonic transducer 46. Similarly, in the example in which a heater is provided in the energy treatment instrument 2, the processor 21 stops the output of the electric energy from the energy output source to the heater in each of the first seal mode and second seal mode. Thus, no electric energy is supplied to the heater in the first seal mode and second seal mode, and therefore no heat will be generated by the heater.

In one example, when the output control in the first seal mode or the output control in the second seal mode ends, no electric energy is supplied to the electrodes 27 and 28, the ultrasonic transducer 46, or the heater, and therefore no treatment energy, such as high-frequency current, ultrasonic vibrations, or the heat of the heater, will be applied to the treatment target. In another example, when the output control in the first seal mode or the output control in the second seal mode ends, the output control is automatically shifted to an incision mode. If this is the case, in the example in which the ultrasonic transducer 46 is provided in the energy treatment instrument 2, the processor 21 causes the energy output source 47 to output the electric energy to the ultrasonic transducer 46 at an incision level (high output level) in the incision mode. This causes the ultrasonic transducer 46 to produce ultrasonic vibrations and to transmit the ultrasonic vibrations to one of the grasping pieces 15 and 16. The transmitted ultrasonic vibrations are applied as the treatment energy to the grasped blood vessel (treatment target), and the blood vessel is incised by frictional heat generated by the ultrasonic vibrations. Similarly, in the example in which the heater is provided in the energy treatment instrument 2, the processor 21 causes the energy output source to output the electric energy at the incision level (high output level) to the heater in the incision mode. The heater thereby generates heat. This heat of the heater is applied as the treatment energy to the grasped blood vessel, and the blood vessel is incised.

Figure 8:
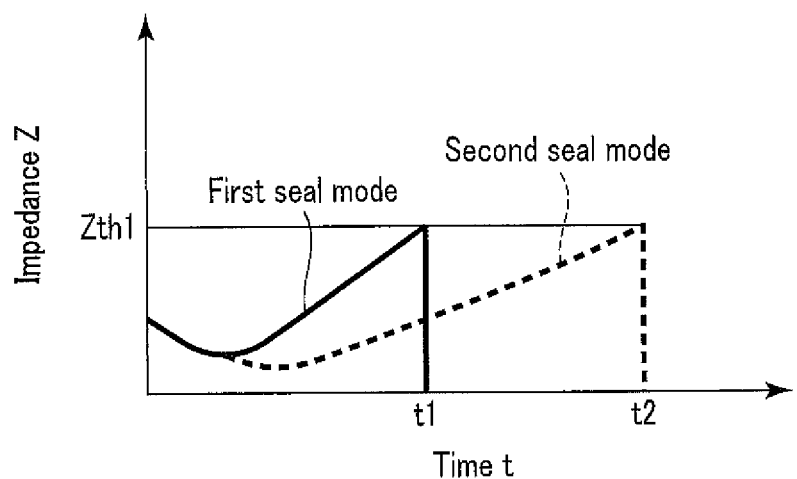
FIG. 8 is a schematic diagram illustrating an example of a variation with time of an impedance between a pair of grasping pieces, in a state in which the processor according to an exemplary embodiment is executing output control in the first seal mode and in the second seal mode.

FIG. 8 is a diagram illustrating an example of a variation with time of the impedance Z between the paired grasping pieces 15 and 16 (i.e. the impedance of the grasped treatment target) in the state in which the processor 21 is executing the output control in the first seal mode and in the second seal mode. In FIG. 8, the ordinate axis indicates the impedance Z, and the abscissa axis indicates time t with reference to the start of the output of the electric energy from the energy output source 32. Furthermore, in FIG. 8, a solid line indicates a variation with time of the impedance Z in the first seal mode, and a broken line indicates a variation with time of the impedance Z in the second seal mode. As shown in FIG. 8, when the output of the electric energy from the energy output source 32 is started and the high-frequency current begins to flow to the blood vessel (treatment target), the impedance Z normally exhibits a behavior of decreasing over time for a certain length of time. After the impedance Z decreases over time to a certain level, the impedance Z normally exhibits a behavior of increasing with time in accordance with the rise in temperature of the treatment target due to the heat generated by the high-frequency current.

As described above, the electric energy that is output from the energy output source 32 in the second seal mode is lower than in the first seal mode according to the present embodiment. For this reason, in comparison with the first seal mode, the amount of heat generated per unit time due to the high-frequency current flowing in the blood vessel (treatment target) is smaller in the second seal mode. Accordingly, the rate of temperature rise of the treatment target (blood vessel) is lower, and the rate of increase of the impedance Z in the state in which the impedance Z increases with time is lower in the second seal mode than in the first seal mode. This means that the time length from the output start of the electric energy from the energy output source 32 to the time of the impedance Z reaching the impedance threshold Zth1 is longer in the second seal mode than in the first seal mode. In fact, in the example of FIG. 8, the impedance Z reaches the impedance threshold Zth1 at time t1 in the first seal mode, whereas the impedance Z reaches the impedance threshold Zth1 at time t2, which is later than time t1, in the second seal mode. As described above, in each of the first seal mode and second seal mode according to the present embodiment, the output of the electric energy from the energy output source 32 is stopped in accordance with the impedance Z reaching or exceeding the impedance threshold Zth1. For this reason, the output time length of the electric energy from the energy output source 32 is longer in the second seal mode than in the first seal mode.

As described above, in comparison to the first seal mode, the output controller 26 (processor 21) reduces the electric energy output from the energy output source 32, and increases the output time length of the electric energy from the energy output source 32 in the second seal mode. This means that, in comparison to the first seal mode, the amount of heat generated per unit of time due to the high-frequency current in the blood vessel is smaller, and the time length of the high-frequency current being supplied to the blood vessel is longer in the second seal mode. That is, in the energy treatment instrument 2, the time length of the treatment energy (high-frequency current) being applied from the energy application section (grasping pieces 15 and 16) to the treatment target (blood vessel) is longer in the second mode (second actuation mode) than in the first mode (first actuation mode). The total amount of treatment energy (high-frequency current) applied to the treatment target in the first seal mode corresponds to, for example, the area defined by the impedance Z indicated by the solid line and time t in FIG. 8. The total amount of treatment energy (high-frequency current) applied to the treatment target in the second seal mode corresponds to, for example, the area defined by the impedance Z indicated by the broken line and time t in FIG. 8. In FIG. 8, the area on the lower side of the impedance Z in the second seal mode, defined by the broken line, is larger than the area on the lower side of the impedance Z in the first seal mode, defined by the solid line. The performance of sealing the blood vessel by the high-frequency current is therefore higher in the second seal mode than in the first seal mode.

In the blood vessel sealing treatment using treatment energy, a blood vessel having a high blood pressure may be grasped between the grasping pieces 15 and 16, and treatment energy such as a high-frequency current may be applied to the grasped blood vessel. As the blood pressure of the grasped blood vessel increases, the sealing treatment using the treatment energy such as a high-frequency current may be affected. Thus, there is a possibility that the performance of sealing the blood vessel, as represented by a pressure resistance value of the sealed blood vessel, may be affected.

According to the present embodiment, the measurement section 41 measures the blood pressure ρ of the site related to the blood vessel (to-be-sealed blood vessel) grasped between the grasping pieces 15 and 16, and the processor 21 controls the output of electric energy from the energy output source 32 or the like, based on the measurement result obtained at the measurement section 41. If the blood pressure ρ is lower than the blood pressure threshold (threshold value) ρth, the output control is executed in the first seal mode. If the blood pressure ρ is greater than or equal to the blood pressure threshold ρth, the output control is executed in the second seal mode. Thus, in comparison to the case in which the blood pressure ρ is lower than the blood pressure threshold ρth, the electric energy that is output from the energy output source 32 is smaller, and the output time length of the electric energy from the energy output source 32 is longer when the blood pressure ρ is greater than or equal to the blood pressure threshold ρth. That is, in the energy treatment instrument 2, the time length of the treatment energy (high-frequency current) supplied from the energy application section (grasping pieces 15 and 16) to the treatment target (blood vessel) is longer in the second mode (second actuation mode), when the blood pressure ρ is greater than or equal to the blood pressure threshold ρth, than in the first mode (first actuation mode), when the blood pressure ρ is lower than the blood pressure threshold ρth. Thus, when the blood pressure ρ is greater than or equal to the blood pressure threshold ρth, the treatment is performed in the second seal mode, in which the energy treatment instrument 2 of the treatment system 1 offers a sealing performance higher than in the first seal mode using the high-frequency current. Thus, the blood vessel can be sealed to the same degree as when the blood pressure ρ is lower than the blood pressure threshold ρth. With the energy treatment instrument 2 of the treatment system 1, the performance of sealing the blood vessel as represented, for example, by the pressure resistance value of the sealed blood vessel (resistance to the blood flow to the sealed region) can be easily maintained even when the blood pressure ρ is greater than or equal to the blood pressure threshold ρth.

If the blood vessel grasped between the grasping pieces 15 and 16 (to-be-sealed blood vessel) has a high blood pressure, the blood pressure ρ of the site related to this blood vessel will also be high. As described above, according to the present embodiment, even if the blood pressure ρ of the site related to the to-be-sealed blood vessel is high, the grasped blood vessel can be suitably sealed by increasing the performance of sealing the blood vessel by using a high-frequency current. That is, even when the blood vessel having a high blood pressure is to be sealed, the blood vessel can be suitably sealed by using the treatment energy such as a high-frequency current, and thereby a suitable treatment performance (sealing performance) can be exhibited.

According another exemplary embodiment, the process performed by the processor 21 in the second seal mode of the output control differs from the process in the previously described embodiment. In the present embodiment, in the first seal mode of the output control, the processor 21 executes the same process as in the previously described embodiment (see FIG. 7). In the same manner as in the first seal mode of the output control, the processor 21 executes the process of steps S111 to S113 in the second seal mode of the output control. In the second seal mode, however, the processor 21 determines whether the detected impedance Z is greater than or equal to an impedance threshold (second impedance threshold) Zth2, instead of executing the process of step S114. Here, the impedance threshold Zth2 is greater than the impedance threshold (first impedance threshold) Zth2. Further, the impedance threshold Zth2 may be set, for example, by the surgeon, or may be stored in the storage medium 22.

If the impedance Z is smaller than the impedance threshold Zth2, the process returns to step S112, where the processes of step S112 and thereafter are sequentially executed. If the impedance Z is greater than or equal to the impedance threshold Zth2, the output controller 26 stops the output of the electric energy (high-frequency electric power) from the energy output source 32. Accordingly, in the second seal mode of the present embodiment, the output of the electric energy from the energy output source 32 is stopped in response to the impedance Z having reached or exceeded the impedance threshold (second impedance threshold) Zth2, which is greater than the impedance threshold (first impedance threshold) Zth1. In this embodiment, the processor 21 controls the output of the electric energy from the energy output source 32, based on the determination result of the blood pressure ρ, and thereby switches the actuation state of the energy treatment instrument 2 between the first mode (first actuation mode) and the second mode (second actuation mode). Furthermore, in this embodiment, the state of the electric energy output from the energy output source 32 is different between the first seal mode and the second seal mode. Thus, in the energy treatment instrument 2, the state of the treatment energy (high-frequency current) applied from the energy application section (grasping pieces 15 and 16) to the grasped treatment target differs between the first mode and the second mode.

Figure 9:
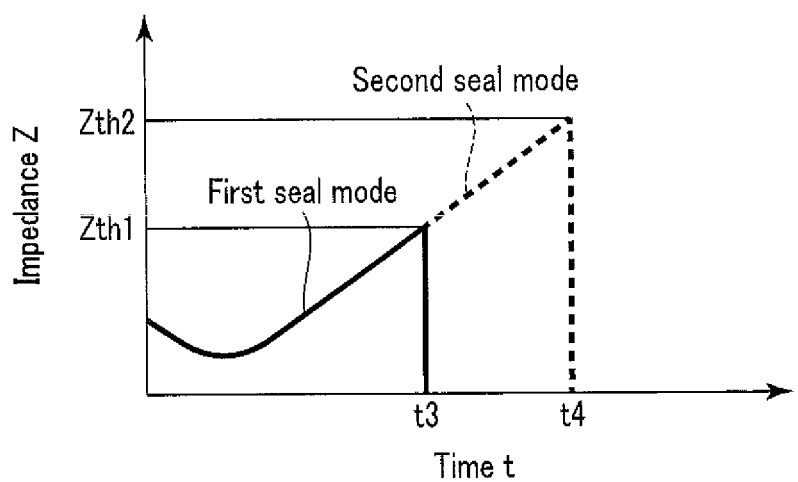
FIG. 9 is a schematic diagram illustrating an example of a variation with time of an impedance between the pair of grasping pieces, in a state in which the processor according to an exemplary embodiment is executing the output control in the first seal mode and in the second seal mode.

FIG. 9 is a diagram illustrating an example of a variation with time of the impedance Z between the paired grasping pieces 15 and 16 in the state in which the processor 21 of this embodiment, is executing the output control in the first seal mode and in the second seal mode. In FIG. 9, the ordinate axis indicates the impedance Z, and the abscissa axis indicates time t with reference to the start of the output of the electric energy from the energy output source 32. Furthermore, in FIG. 9, a solid line indicates a variation with time of the impedance Z in the first seal mode, and a broken line indicates a variation with time of the impedance Z in the second seal mode.

As described above, in the present embodiment, the output of the electric energy from the energy output source 32 is stopped in response to the impedance Z having reached or exceeded the impedance threshold Zth1 in the first seal mode. On the other hand, in the second seal mode, the output of the electric energy from the energy output source 32 is stopped in response to the impedance Z having reached or exceeded the impedance threshold Zth2. The impedance threshold Zth2 is greater than the impedance threshold Zth1. Thus, the output time length of the electric energy from the energy output source 32 is longer in the second seal mode than in the first seal mode. In fact, in the example of FIG. 9, the output of the electric energy is stopped at time t3 in the first seal mode, whereas the output of the electric energy is stopped at time t4, which is later than time t3 in the second seal mode.

As described above, in the present embodiment, the output controller 26 (processor 21) sets the impedance threshold (Zth2), which serves as the reference for stopping the output, to be larger and the output time length of the electric energy from the energy output source 32 to be longer, in the second seal mode than in the first seal mode. That is, in the energy treatment instrument 2 of the present embodiment, the time length of the treatment energy (high-frequency current) being applied from the energy application section (grasping pieces 15 and 16) to the treatment target (blood vessel) is longer in the second mode (second actuation mode), in which the blood pressure ρ is greater than or equal to the blood pressure threshold ρth, than in the first mode (first actuation mode), in which the blood pressure ρ is lower than the blood pressure threshold ρth. Thus, in comparison to the first seal mode, the time length during which the high-frequency current is applied to the blood vessel is longer, and the total amount of treatment energy (high-frequency current) applied to the blood vessel is larger in the second seal mode, and the performance of sealing the blood vessel by the high-frequency current is thereby enhanced. Accordingly, when the blood pressure ρ is greater than or equal to the blood pressure threshold ρth, the treatment is performed in the second seal mode, in which the performance of the energy treatment instrument 2 of the treatment system 1 sealing the blood vessel by use of the high-frequency current is higher than the first seal mode. Thus, the blood vessel can be sealed to substantially the same degree as when the blood pressure ρ is lower than the blood pressure threshold ρth. With the energy treatment instrument 2 of the treatment system 1, the performance of sealing the blood vessel as represented, for example, by the pressure resistance value of the sealed blood vessel (resistance to the blood flow to the sealed region) can be easily maintained even when the blood pressure ρ is greater than or equal to the blood pressure threshold ρth.

As one embodiment, the previously described embodiments may be combined. If this is the case, the processor 21 reduces the electric energy output from the energy output source 32, and sets the impedance threshold (Zth2), which serves as the reference for stopping the output, to be larger in the second seal mode, in comparison to the first seal mode. Since the state of the electric energy output from the energy output source 32 differs between the first seal mode and second seal mode in this embodiment, the state of the treatment energy (high-frequency current) applied from the energy application section (grasping pieces 15 and 16) to the grasped treatment target differs between the first mode and the second mode in the energy treatment instrument 2.

Figure 10:
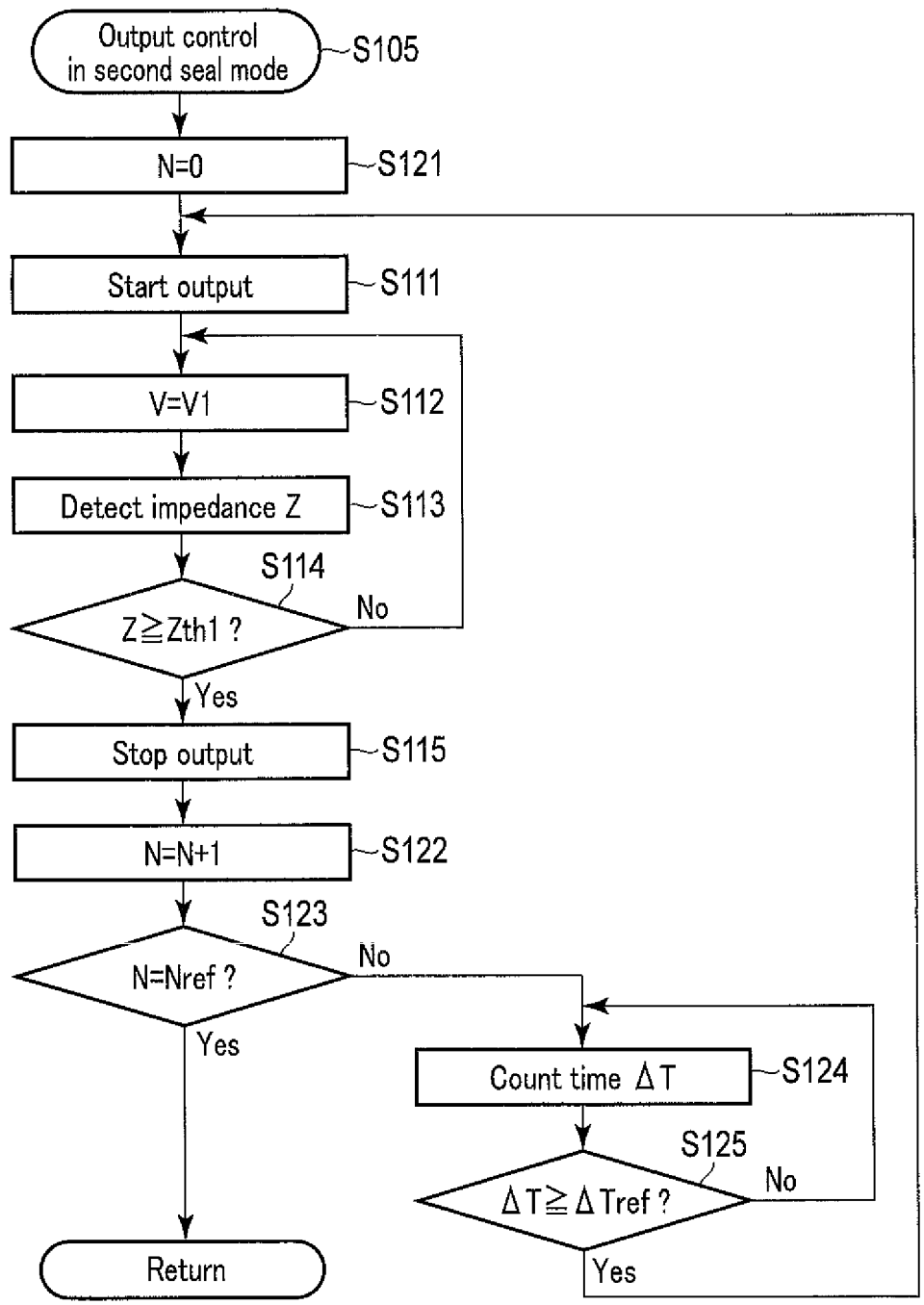
FIG. 10 is a flowchart illustrating a process in the second seal mode of the output control executed by the processor according to an exemplary embodiment.

Additionally, in another exemplary embodiment, in the output control in the second seal mode, the processor 21 executes a process illustrated in FIG. 10. In the present embodiment, in the first seal mode of the output control, the processor 21 executes the same process as in the exemplary embodiment shown in FIG. 7. In this embodiment, the number of outputs N is defined as a parameter for the electric energy from the energy output source 32 in the second seal mode of the output control. In the second seal mode of the output control, the processor 21 sets 0 as a default value for the number of outputs N (step S121). In the same manner as in the first seal mode of the output control, the processor 21 executes the processes of steps S111 to S115.

When the output of the electric energy from the energy output source 32 is stopped by the process at step S115, the processor 21 increments the number of outputs N by 1 (step S122). Then, the processor 21 determines whether the incremented number of outputs N is equal to a reference number of times Nref (step S123). The reference number of times Nref is any natural number greater than or equal to 2, which may be set, for example, by the surgeon, or may be stored in the storage medium 22. If the number of outputs N is equal to the reference number of times Nref, or in other words, if the number of outputs N has reached the reference number of times Nref (Yes at step S123), the processor 21 terminates the output control in the second seal mode. In this manner, the state in which the output of the electric energy from the energy output source 32 is stopped is maintained.

Here, the time elapsed from the latest time point (time point 0) among the time points at which the output of the electric energy from the energy output source 32 is stopped by the process at step S115 is defined as ΔT. If the number of outputs N is not equal to the reference number of times Nref, or in other words, if the output number of times N has not reached the reference number of times Nref (No at step S123), the processor 21 counts the time ΔT (step S124). Then, the processor 21 determines whether the counted time ΔT is greater than or equal to a reference time ΔTref (step S125). The reference time ΔTref may be, for example, 10 msec, which may be set, for example, by the surgeon, or may be stored in the storage medium 22.

If the time ΔT is shorter than the reference time ΔTref (No at step S125), the process returns to step S124, and the processes of step S124 and thereafter are sequentially executed. Specifically, the state in which the output of the electric energy from the energy output source 32 is stopped is maintained, and the time ΔT continues to be counted. If the time ΔT is the reference time ΔTref or greater (Yes at step S125), the process returns to step S111, and the processes of step S111 and thereafter are sequentially executed. In other words, the output of the electric energy from the energy output source 32 is resumed.

With the above process, in the second seal mode of the output control, the output controller 26 of the processor 21 stops the output of the electric energy after starting the output of the electric energy from the energy output source 32. Furthermore, after suspending the output of the electric energy from the energy output source 32, the output controller 26 resumes the output of the electric energy. That is, in the second seal mode, when the reference time ΔTref has passed after the time point of suspending the output of the electric energy from the energy output source 32, the electric energy is output once again from the energy output source 32. During the output control in the second seal mode, the processor 21 causes the energy output source 32 to intermittently output the electric energy for the reference number of times Nref (multiple times). In this embodiment, the processor 21 controls the output of the electric energy from the energy output source 32, based on the determination result of the blood pressure ρ, and thereby switches the actuation state of the energy treatment instrument 2 between the first mode (first actuation mode) and the second mode (second actuation mode). Since the state of the electric energy output from the energy output source 32 differs between the first seal mode and second seal mode in this embodiment, the state of the treatment energy (high-frequency current) applied from the energy application section (grasping pieces 15 and 16) to the grasped treatment target differs between the first mode and the second mode in the energy treatment instrument 2.

FIG. 11 is a diagram illustrating an example of a variation with time of the impedance Z between the paired grasping pieces 15 and 16 in the state in which the processor 21 of this embodiment, is executing the output control in the first seal mode and in the second seal mode. In FIG. 11, the ordinate axis indicates the impedance Z, and the abscissa axis indicates time t with reference to the start of the output of the electric energy from the energy output source 32. Furthermore, in FIG. 11, a solid line indicates a variation with time of the impedance Z in the first seal mode, and a broken line indicates a variation with time of the impedance Z in the second seal mode. In the example shown in FIG. 11, the output of the electric energy from the energy output source 32 is stopped at time t5, in response to the impedance Z having reached the impedance threshold Zth1, in each of the first seal mode and second seal mode.

As described above, in the present embodiment, the electric energy is intermittently output from the energy output source 32 for multiple times (reference number of times Nref) in the second seal mode. In the second seal mode in the example shown in FIG. 11, the output of the electric energy from the energy output source 32 is resumed at time t6 when the reference time ΔTref has elapsed from time t5 at which the output was stopped. Here, the impedance Z is smaller than the impedance threshold Zth1. At time t7 after the time t6 (at which the output of the electric energy was resumed), in response to the impedance Z having reached the impedance threshold Zth1, the output of the electric energy from the energy output source 32 is stopped once again. In the example of FIG. 11, the reference number of times Nref is 2.

As described above, in the present embodiment, the output controller 26 (processor 21) resumes the output of the electric energy after suspending the output in the second seal mode. The output time length of the electric energy from the energy output source 32 therefore becomes longer in the second seal mode than in the first seal mode, as a result of which the time length of the high-frequency current being applied to the blood vessel becomes longer in the second seal mode than in the first seal mode. That is, in the energy treatment instrument 2 of the present embodiment, the time length of the treatment energy (high-frequency current) being applied from the energy application section (grasping pieces 15 and 16) to the treatment target (blood vessel) is longer in the second mode (second actuation mode), in which the blood pressure ρ is greater than or equal to the blood pressure threshold ρth, than in the first mode (first actuation mode), in which the blood pressure ρ is lower than the blood pressure threshold ρth. For this reason, the performance of sealing the blood vessel by the high-frequency current is higher in the second seal mode than in the first seal mode. Accordingly, when the blood pressure ρ is greater than or equal to the blood pressure threshold ρth, the treatment is performed in the second seal mode, in which the performance of sealing the blood vessel using the high-frequency current of the energy treatment instrument 2 of the treatment system 1 is higher than in the first seal mode. Thus, the blood vessel can be sealed to substantially the same degree as when the blood pressure ρ is lower than the blood pressure threshold ρth. With the energy treatment instrument 2 of the treatment system 1, the performance of sealing the blood vessel as represented, for example, by the pressure resistance value of the sealed blood vessel (resistance to the blood flow to the sealed region) can be easily maintained even when the blood pressure ρ is greater than or equal to the blood pressure threshold ρth.

In another exemplary embodiment, the processor 21 executes a process illustrated in FIG. 12 in the second seal mode of the output control. In the first seal mode of the output control, the processor 21 executes the same process as in the embodiment shown in FIG. 7. Furthermore, in the second seal mode of the output control, the processor 21 executes the processes of steps S111 through S115 in the same manner as in the first seal mode of the output control.

In the second seal mode, when the output of the electric energy from the energy output source 32 is stopped as a result of the process in step S115, the output controller 26 of the processor 21 starts the output of the electric energy from the energy output source 47 to the ultrasonic transducer 46 (step S131). Here, the energy output source 47 outputs the electric energy at a seal level having a low output level. That is, when the electric energy is output at the seal level, the output level is lower than the output of the electric energy at the above-described incision level. Thus, the electric energy supplied to the ultrasonic transducer 46 is lower, and the amplitude of the ultrasonic vibrations transferred to one of the grasping pieces 15 and 16 is smaller, in the output at the seal level than in the output at the incision level. Because the amount of frictional heat generated by the ultrasonic vibrations is small in the output at the seal level, the grasped blood vessel will not be incised by the frictional heat, but will only be sealed. In FIG. 12, the "HF output" denotes the high-frequency output of the electric energy from the energy output source 32 to the electrodes 27 and 28, and the "US output" denotes the ultrasonic output of the electric energy from the energy output source 47 to the ultrasonic transducer 46.

Here, a time (elapsed time) ΔT' is defined with reference to the time point of starting the output of the electric energy from the energy output source 47 at the seal level as a result of the process in step S131 (i.e., the time point of stopping the output from the energy output source 32 as a result of the process in step S115) being 0. When the output of the electric energy is started from the energy output source 47 at the seal level, the processor 21 starts counting the time ΔT' (step S132). The processor 21 determines whether the counted time ΔT' is greater than or equal to a reference time ΔT' ref (step S133). The reference time ΔT' ref may be set, for example, by the surgeon, or may be stored in the storage medium 22.

If the time ΔT' is shorter than the reference time ΔT' ref (No at step S133), the process returns to step S132, and the processes of step S132 and thereafter are sequentially executed. That is, the time ΔT' continues to be counted. If the time ΔT' is greater than or equal to the reference time ΔT' ref (Yes at step S133), the output controller 26 terminates the output of the electric energy from the energy output source 47 at the seal level (step S134). Here, the output of the electric energy from the energy output source 47 to the ultrasonic transducer 46 may be stopped. Alternatively, the output control may be automatically shifted to the incision mode so as to automatically change to a state in which the electric energy is output to the ultrasonic transducer 46 at the incision level (high output level). In one example, instead of the processes of steps S132 and S133, the output controller 26 may terminate the output of the electric energy at the seal level from the energy output source 47, in response to the release of the operation input of the operation button (energy operation input section) 18 (i.e., the operation input being turned off).

As described above, in the present embodiment, when the output controller 26 (processor 21) stops the output of the electric energy to the electrodes 27 and 28 in the second seal mode, the output controller 26 starts the output of the electric energy to the ultrasonic transducer 46. That is, the processor 21 controls the output of the electric energy from the energy output sources 32 and 47, based on the determination result of the blood pressure ρ, thereby switching the actuation state of the energy treatment instrument 2 between the first mode (first actuation mode) and the second mode (second actuation mode). In the present embodiment, the electric energy is output from the energy output source 47 in the second seal mode only. Therefore, in the energy treatment instrument 2, the state of the treatment energy (high-frequency current and ultrasonic vibrations) applied from the energy application section (grasping pieces 15 and 16) to the grasped treatment target differs between the first mode and the second mode. For this reason, in the second seal mode, even after the output of the electric energy to the electrodes 27 and 28 is stopped, the ultrasonic vibrations (frictional heat) seal the grasped blood vessel. That is, in the second seal mode, even in the state in which the impedance Z is increased, causing a resistance to the high-frequency current flow in the blood vessel, the blood vessel can still be sealed by the frictional heat generated by the ultrasonic vibrations. In this manner, in comparison to the first seal mode, the performance of sealing the blood vessel by the treatment energy is enhanced in the second seal mode. Accordingly, when the blood pressure ρ is greater than or equal to the blood pressure threshold ρth, the treatment is performed in the second seal mode, in which the performance of sealing the blood vessel using the treatment energy of the energy treatment instrument 2 of the treatment system 1 is higher than in the first seal mode. Thus, the blood vessel can be sealed to substantially the same degree as when the blood pressure ρ is lower than the blood pressure threshold ρth. With the energy treatment instrument 2 of the treatment system 1, the performance of sealing the blood vessel as represented, for example, by the pressure resistance value of the sealed blood vessel (resistance to the blood flow to the sealed region) can be easily maintained even when the blood pressure ρ is greater than or equal to the blood pressure threshold ρth.

In one embodiment, when the output of the electric energy from the energy output source 32 is stopped by the process in step S115 in the second seal mode, the output controller 26 of the processor 21 starts the output of the electric energy to the heater. At this time, the electric energy is output at the seal level having a lower output level than the above-described incision level. Thus, the electric energy supplied to the heater as the output at the seal level is smaller than the output at the incision level. With a small amount of heat generated by the heater as the output at the seal level, the grasped blood vessel is not incised by the heat of the heater, and therefore only sealing of the blood vessel is performed. In this embodiment, the blood vessel is sealed in the second seal mode by the heat of the heater in addition to the high-frequency current. That is, in the present embodiment, the state of the treatment energy (the high-frequency current and the heat of the heater) applied from the energy application section (grasping pieces 15 and 16) to the grasped treatment target differs between the first mode and the second mode in the energy treatment instrument 2. The performance of sealing the blood vessel by the treatment energy is therefore higher in the second seal mode than in the first seal mode. Thus, the same function and advantageous effects as in the previously described embodiment can be obtained.

The output control of the electric energy, in which the sealing performance of the blood vessel by the treatment energy is increased when the blood pressure ρ is greater than or equal to the blood pressure threshold ρth, in comparison to when the blood pressure ρ is lower than the blood pressure threshold ρth, may be adopted for an example in which a high-frequency current is not applied to the blood vessel, but only the treatment energy other than the high-frequency current (e.g., the ultrasonic vibration and the heat of the heater) is applied to the blood vessel. For instance, in one embodiment, in which the electric energy is output to the ultrasonic transducer 46 at the seal level so as to seal the blood vessel by using only the ultrasonic vibrations, the processor 21 reduces the electric energy to be output from the energy output source 47 to the ultrasonic transducer 46, and increases the output time length of the electric energy to the ultrasonic transducer 46 in the second seal mode (the second mode of the energy treatment instrument 2), in comparison to the first seal mode (the first mode of the energy treatment instrument 2). In this manner, the time length of the ultrasonic vibrations being applied to the blood vessel is longer, and the performance of sealing the blood vessel by the ultrasonic vibrations is higher in the second seal mode (when the blood pressure ρ is greater than or equal to the blood pressure threshold ρth) than in the first seal mode (when the blood pressure ρ is lower than the blood pressure threshold ρth). Furthermore, in one embodiment, in which the electric energy is output to the heater at the seal level and the blood vessel is sealed by using only the heat of the heater, the processor 21 reduces the electric energy to be output from the energy output source to the heater, and increases the output time length of the electric energy to the heater in the second seal mode, in comparison with the first seal mode. As a result, the time length of the heat of the heater being applied to the blood vessel becomes longer, and the performance of sealing the blood vessel by the heat of the heater becomes higher in the second seal mode (when the blood pressure $\rho$ is greater than or equal to the blood pressure threshold $\rho$th) than in the first seal mode (when the blood pressure $\rho$ is lower than the blood pressure threshold $\rho$th). With the energy treatment instrument 2 of the treatment system 1, the performance of sealing the blood vessel as represented, for example, by the pressure resistance value of the sealed blood vessel (resistance to the blood flow to the sealed region) can be easily maintained even when the blood pressure $\rho$ is greater than or equal to the blood pressure threshold $\rho$th.

In one embodiment, whether the processor 21 executes the output control in the first seal mode or in the second seal mode may be determined, for example, by the surgeon. In this embodiment, for example, two operation buttons, which serve as an energy operation input section, may be provided so that, when an operation is input from one of the operation buttons, the processor 21 (output controller 26) executes the output control of the electric energy in the first seal mode, and the energy treatment instrument 2 is actuated in the first mode (first actuation mode) for coagulating the treatment target. When an operation is input from the other operation button, the processor 21 executes the output control of the electric energy in the second seal mode, in which the performance of sealing the blood vessel by the treatment energy is higher than in the first seal mode. The energy treatment instrument 2 is thereby actuated in the second mode (second actuation mode) in which the treatment target is coagulated and in which the state of the treatment energy applied to the treatment target differs from the first mode. In the second mode, the performance of coagulating the treatment target by the treatment energy (the performance of sealing the blood vessel by the treatment energy) is higher than in the first mode. In this embodiment, a notification section (not shown) configured to notify whether the blood pressure $\rho$ of the site related to the grasped blood vessel is lower than the blood pressure threshold $\rho$th may be provided in the control device 3. In one example, the notification section is an LED, and the LED is turned on when the blood pressure $\rho$ is greater than or equal to the blood pressure threshold $\rho$th. In another example, the notification section may be a buzzer, a display screen, or the like.

In another embodiment, the notification section may be a display screen or the like configured to notify the measurement result of the blood pressure $\rho$ obtained by the measurement section 41. In this modification, the surgeon determines, whether or not the blood pressure $\rho$ is lower than the blood pressure threshold $\rho$th, based on the information notified by the notification section. Then, the surgeon determines which of the two operation buttons is to be operated to execute the operation input, and selects whether the processor 21 executes the output control in the first seal mode or in the second seal mode.

Figure 13:
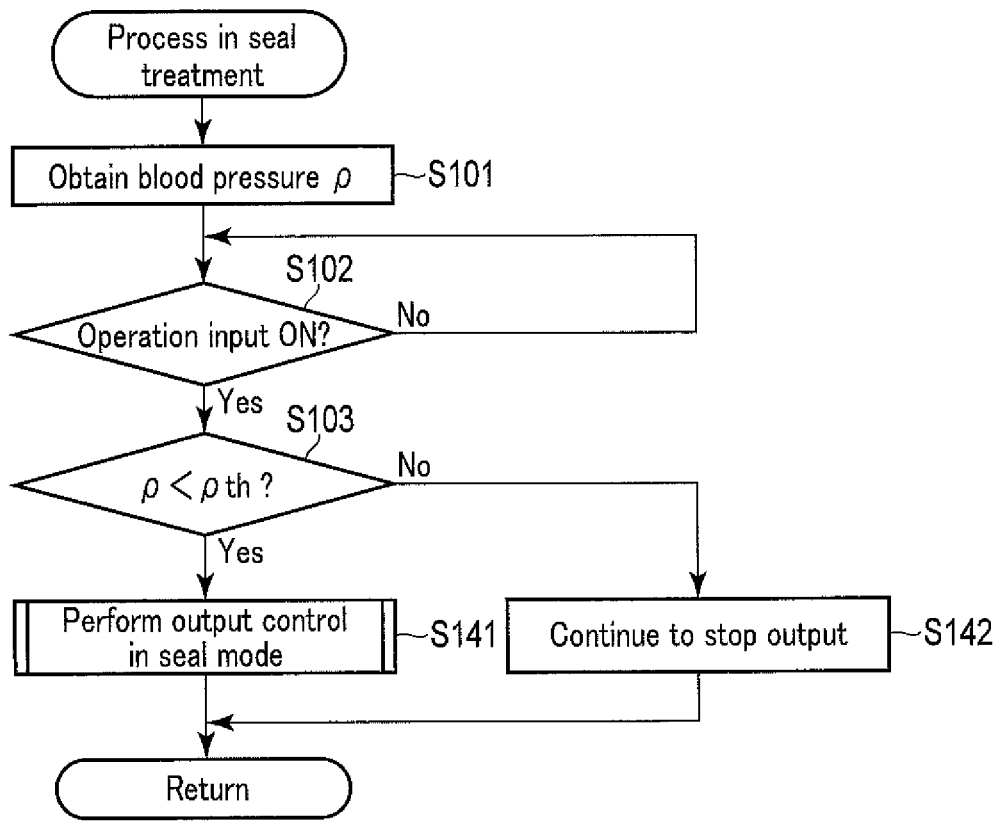
FIG. 13 is a flowchart illustrating a process executed in the seal treatment of the blood vessel by the processor using the treatment system according to an exemplary embodiment.

In another exemplary embodiment, in the seal treatment of the blood vessel, the processor 21 executes a process illustrated in FIG. 13. In the same manner as the above-described embodiment, the processor 21 executes the processes of steps S101 to S103 in the seal treatment of the blood vessel, in the present embodiment. When the blood pressure $\rho$ is lower than the blood pressure threshold $\rho$th (Yes at step S103), the processor 21 executes the output control of the electric energy in the seal mode (step S141). In the output control in the seal mode, the processor 21 executes, for example, the same process as the output control in the first seal mode of the exemplary embodiment shown in FIG. 7. The processor 21 executes the output control of the electric energy in the seal mode, and thereby the energy treatment instrument 2 is actuated in the first mode for coagulating the grasped treatment target (sealing the blood vessel). If the blood pressure $\rho$ is greater than or equal to the blood pressure threshold $\rho$th (No at step S103), the processor 21 continues to stop the output of the electric energy, whether or not an operation is input from the operation button 18 (step S142). Here, the energy treatment instrument 2 is actuated in the second mode. That is, the output of the electric energy from the energy output sources 32 and 47 continues to be stopped. Thus, when the blood pressure $\rho$ is greater than or equal to the blood pressure threshold $\rho$th, no treatment energy such as high-frequency current is applied to the grasped blood vessel even if an operation is input from the operation button 18. In this embodiment, the processor 21 controls the output of the electric energy from the energy output source 32 based on the determination result of the blood pressure $\rho$, and thereby switches the actuation state of the energy treatment instrument 2 between the first mode (first actuation mode) and the second mode (second actuation mode). In this embodiment, the output of the electric energy from the energy output sources 32 and 47 is stopped in the second mode, and therefore the state of the treatment energy (high-frequency current, etc.) applied from the energy application section (grasping pieces 15 and 16) to the grasped treatment target in the energy treatment instrument 2 differs between the first mode and the second mode.

With the output control as described above in the present embodiment, no treatment energy is applied to a blood vessel even when the blood vessel having a high blood pressure is grasped between the grasping pieces 15 and 16. The treatment energy is applied to the blood vessel only in the state in which the sealing performance will be barely affected, for example, when the blood vessel having a blood pressure that is not too high is grasped between the grasping pieces 15 and 16. Thus, the blood vessel is suitably sealed by using the treatment energy such as a high-frequency current, and a suitable treatment performance (sealing performance) can be achieved.

In yet another embodiment, the surgeon may decide whether or not the electric energy should be output in the seal mode. In this embodiment, the above-described notification section may be provided in, for example, the control device 3. When it is notified or determined that the blood pressure $\rho$ is lower than the blood pressure threshold $\rho$th, the surgeon inputs an operation from the operation button 18 so that the processor 21 executes the output control in the seal mode. The electric energy is thereby output from the energy output sources 32 and 47, and the energy treatment instrument 2 is actuated in the first mode (first actuation mode). On the other hand, when it is notified or determined that the blood pressure $\rho$ is greater than or equal to the blood pressure threshold $\rho$th, the surgeon will not input any operation from the operation button 18. Thus, without any electric energy output from the energy output sources 32 and 47, the energy treatment instrument 2 is actuated in the second mode (second actuation mode) that is different from the first mode.

Second Embodiment

Next, an exemplary embodiment will be described with reference to FIGS. 14 to 16.

Figure 14:
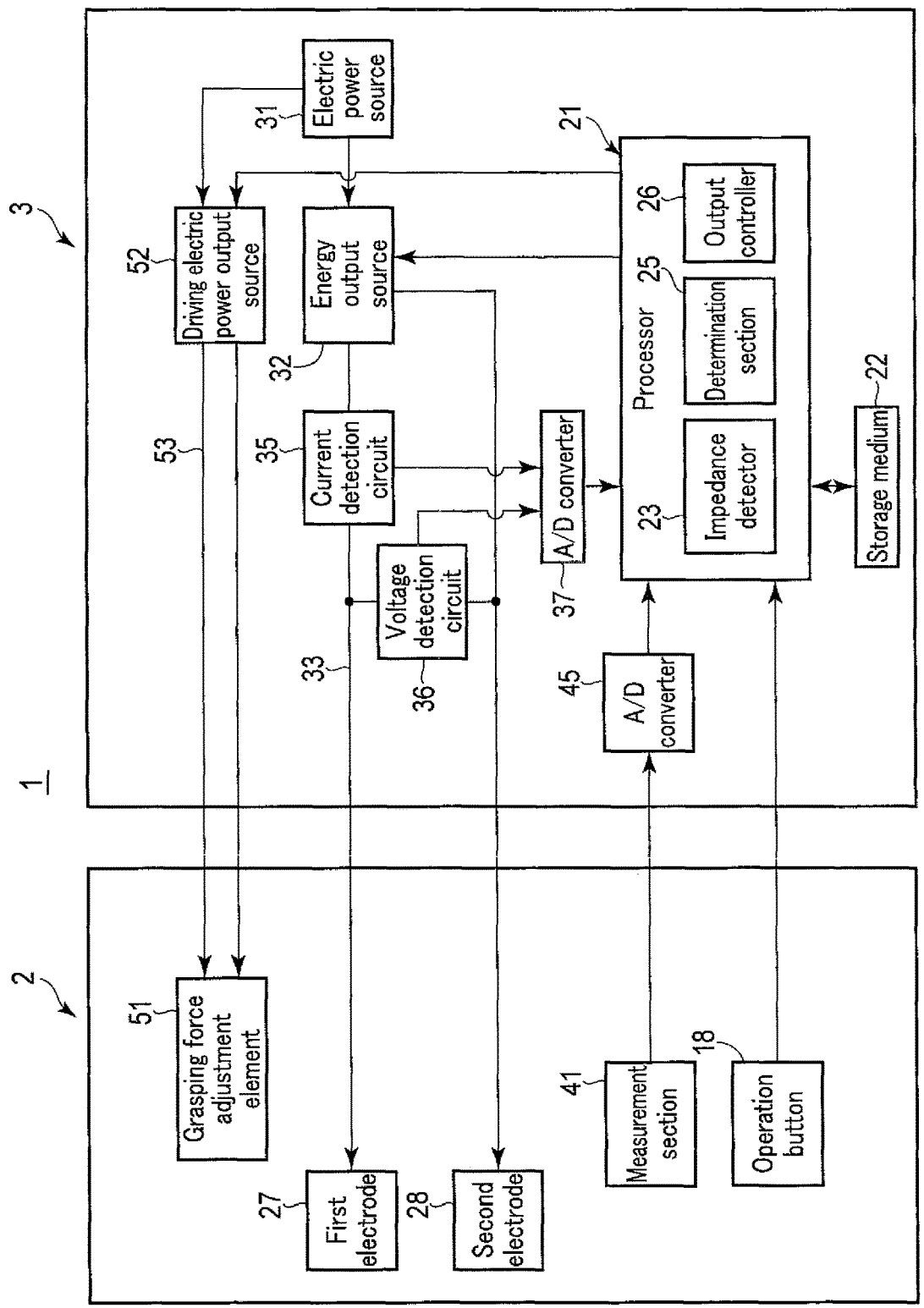
FIG. 14 is a block diagram illustrating a control configuration in a treatment system according to an exemplary embodiment.

FIG. 14 is a diagram illustrating a control configuration in a treatment system 1 according to the present embodiment. In the present embodiment, a grasping force adjustment element (grasping force adjuster) 51 is provided in the energy treatment instrument 2, as illustrated in FIG. 14. A grasping force acting on the treatment target (blood vessel) between the grasping pieces 15 and 16 varies in accordance with a driving state of the grasping force adjustment element 51. That is, the grasping force acting on the treatment target between the grasping pieces 15 and 16 is adjusted by the grasping force adjustment element 51. In addition, in this embodiment, a driving electric power output source 52 is provided in the control device 3. The driving electric power output source 52 is electrically connected to the grasping force adjustment element 51 via an electricity supply path 53 extending inside the cable 10. Here, the driving electric power output source 52 may be formed integrally with the above-described energy output sources 32 and 47, or may be formed separately from the energy output sources 32 and 47.

The driving electric power output source 52 includes a converter circuit, an amplifier circuit, and the like, and converts the electric power from the electric power source 31 to the driving electric power for the grasping force adjustment element 51. The driving electric power output source 52 outputs the converted driving electric power, and the output driving electric power is supplied to the grasping force adjustment element 51 through the electricity supply path 53. The processor 21 controls the driving of the driving electric power output source 52, and controls the output of the driving electric power from the driving electric power output source 52. In this manner, the supply of the driving electric power to the grasping force adjustment element 51 is controlled, and the driving of the grasping force adjustment element 51 is controlled. According to the present embodiment, in accordance with the driving state of the grasping force adjustment element 51, the actuation state of the energy treatment instrument 2 is switched between the first mode (first actuation mode) and the second mode (second actuation mode). According to the present embodiment, the grasping force acting on the treatment target (blood vessel) between the grasping pieces 15 and 16 differs between the first mode and the second mode.

Figure 15:
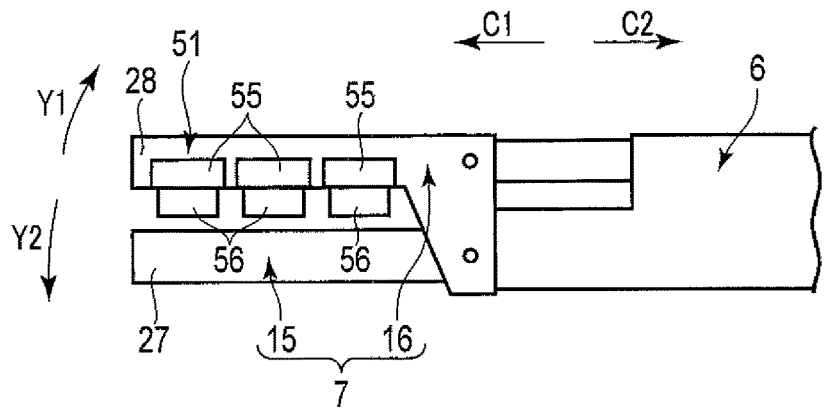
FIG. 15 is a schematic view illustrating an example of a grasping force adjustment element according to an exemplary embodiment.
Figure 16:
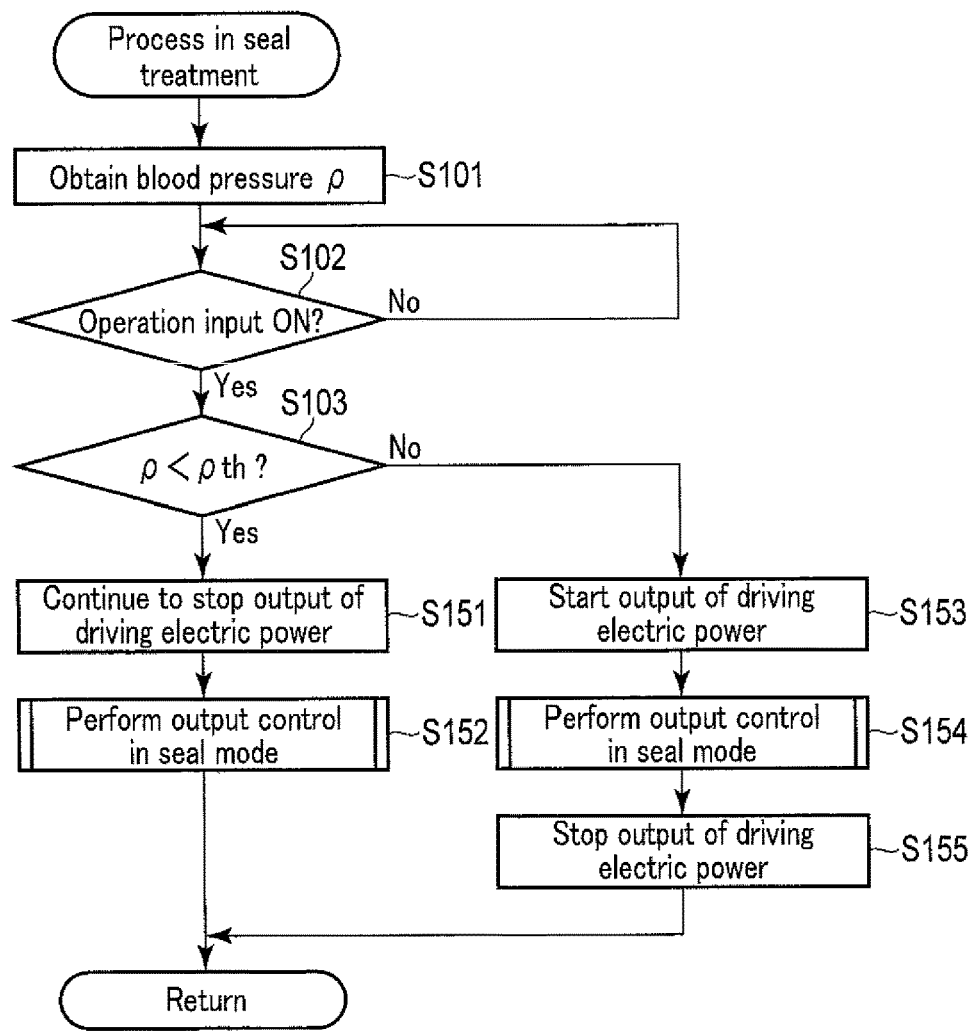
FIG. 16 is a flowchart illustrating a process executed by the processor in the seal treatment of the blood vessel using the treatment system according to an exemplary embodiment.

FIG. 15 is a diagram illustrating an example of the grasping force adjustment element 51. In the example illustrated in FIG. 15, a heater 55 and a volume change portion 56 are provided as the grasping force adjustment element 51 in the second grasping piece 16. The volume change portion 56 is formed of an electrically insulating material such as parylene, nylon, or ceramics. By closing the grasping pieces 15 and 16 relative to each other, the volume change portion 56 is brought into contact with the first grasping piece 15 (first electrode 27). In the state in which the volume change portion 56 is in contact with the first grasping piece 15, the electrodes 27 and 28 are spaced apart from each other, and are prevented from being in a contact with each other by the volume change portion 56. The volume change portion 56 is formed of a material having a high thermal expansion coefficient.

With the driving electric power output from the driving electric power output source 52 to the heater 55, the grasping force adjustment element 51 is driven, and heat is generated by the heater 55. With the heat generated by the heater 55, the temperature of the volume change portion 56 rises, as a result of which the volume change portion 56 expands (the volume of the volume change portion 56 increases). Because of the volume change portion 56 expanding in the state in which the blood vessel (treatment target) is grasped between the grasping pieces 15 and 16, the distance between the grasping pieces 15 and 16 decreases, and the grasping force acting on the treatment target between the grasping pieces 15 and 16 increases. In this example, the heat generated by the heater 55 is not used for coagulation or incision of the treatment target.

In another example, a Peltier element may be provided in place of the heater 55. With this arrangement, the driving electric power is output from the driving electric power output source 52 to the Peltier element, and the Peltier element thereby transfers the heat to the volume change portion 56 side. With the heat transferred by the Peltier element, the temperature of the volume change portion 56 rises, as a result of which the volume change portion 56 expands. Thus, as described above, in the state in which the blood vessel (treatment target) is grasped between the grasping pieces 15 and 16, the distance between the grasping pieces 15 and 16 decreases, and the grasping force of the treatment target between the grasping pieces 15 and 16 increases.

Next, the function and advantageous effects of the present embodiment will be described. FIG. 16 is a flowchart illustrating the process executed by the processor 21 in the seal treatment of the blood vessel using the treatment system 1 of the present embodiment. In the present embodiment, the processor 21 executes the processes of steps S101 to S103 in the seal treatment of the blood vessel in the same manner as the above-described embodiment and the like. When the blood pressure ρ is lower than the blood pressure threshold ρth (Yes at step S103), the processor 21 continues to stop the output of the driving electric power from the driving electric power output source 52 to the grasping force adjustment element 51 (step S151). The grasping force adjustment element 51 is therefore not driven, and the volume change portion 56 does not expand. The grasping force of the treatment target between the grasping pieces 15 and 16 is thereby maintained. Furthermore, the processor 21 executes the output control of the electric energy from the energy output source 32 or the like in the seal mode (step S152). In the output control in the seal mode, the processor 21 executes, for example, the same process as the output control in the first seal mode of the embodiment shown in FIG. 7. In the state in which the output of the driving electric power from the driving electric power output source 52 to the grasping force adjustment element (grasping force adjuster) 51 is stopped by the processor 21 and the grasping force adjustment element 51 is not driven, the energy treatment instrument 2 is actuated in the first mode (first actuation mode) for coagulating the grasped treatment target (sealing the blood vessel).

On the other hand, when the blood pressure ρ is greater than or equal to the blood pressure threshold ρth (No at step S103), the processor 21 starts to output the driving electric power from the driving electric power output source 52 to the grasping force adjustment element 51 (step S153). Thus, the grasping force adjustment element 51 is driven, and the volume change portion 56 expands. The grasping force acting on the treatment target between the grasping pieces 15 and 16 thereby increases. The processor 21 executes the output control of the electric energy from the energy output source 32 or the like in the seal mode (step S154). In the output control in the seal mode, the processor 21 executes, for example, the same process as the output control in the first seal mode of the embodiment shown in FIG. 7. When the output control in the seal mode ends, the processor 21 stops the output of the driving electric power from the driving electric power output source 52 to the grasping force adjustment element 51 (step S155). In the state in which the processor 21 causes the driving electric power output source 52 to output the driving electric power to the grasping force adjustment element 51 and thereby drives the grasping force adjustment element 51, the energy treatment instrument 2 is actuated in the second mode (second actuation mode), which is different from the first mode and is for coagulating the grasped treatment target (sealing the blood vessel). As described above, in the present embodiment, the processor 21 controls the output of the driving electric power from the driving electric power output source 52 based on the determination result of the blood pressure $\rho$, thereby switching the actuation state of the energy treatment instrument 2 between the first mode (first actuation mode) and second mode (second actuation mode). In the energy treatment instrument 2, the driving state of the grasping force adjustment element 51 differs between the first mode and the second mode. Thus, the grasping force of the treatment target (blood vessel) between the grasping pieces 15 and 16 differs between the first mode and the second mode.

In the present embodiment, under the control by the processor 21 as described above, the processor 21 increases the grasping force of the blood vessel (treatment target) between the grasping pieces 15 and 16 when the blood pressure $\rho$ is greater than or equal to the blood pressure threshold $\rho$th, in comparison to when the blood pressure $\rho$ is lower than the blood pressure threshold $\rho$th. That is, in the energy treatment instrument 2, the grasping force acting on the blood vessel (treatment target) between the grasping pieces 15 and 16 is larger in the second mode (second actuation mode) than in the first mode (first actuation mode). For this reason, even when a blood vessel having a high blood pressure is grasped between the grasping pieces 15 and 16, the grasped blood vessel can be suitably sealed by increasing the grasping force to grasp the blood vessel between the grasping pieces 15 and 16. That is, even when a blood vessel having a high blood pressure is to be sealed, the blood vessel can be suitably sealed using the treatment energy, and a suitable treatment performance (sealing performance) can be achieved.

The grasping force adjustment element 51 is not limited to the above configuration. In one embodiment, for example, an electric motor and an abutment member are provided as the grasping force adjustment element 51. If this is the case, the handle 12 is brought into contact with the abutment member by closing the handle 12 relative to the grip 11, and the handle 12 is closed relative to the grip 11 up to come to a position at which the handle 12 abuts on the abutment member. The processor 21 (output controller 26) controls the output of the driving electric power from the driving electric power output source 52 to the electric motor, and thereby controls the driving of the electric motor. When the electric motor is driven, the abutment member is moved, and the position of the abutment member is changed. This changes the stroke of the handle at a time of closing the handle 12 relative to the grip 11. In the present embodiment, the processor 21 adjusts the position of the abutment member, based on the blood pressure $\rho$ so that the stroke of the handle 12 for closing can be increased when the blood pressure $\rho$ is greater than or equal to the blood pressure threshold $\rho$th, in comparison to the case in which the blood pressure $\rho$ is lower than the blood pressure threshold $\rho$th. Furthermore, in this embodiment, the grasping force for grasping the blood vessel (treatment target) between the grasping pieces 15 and 16 increases when the blood pressure $\rho$ is greater than or equal to the blood pressure threshold $\rho$th (the second mode of the energy treatment instrument 2), in comparison to when the blood pressure $\rho$ is lower than the blood pressure threshold $\rho$th (the first mode of the energy treatment instrument 2).

For an arrangement in which one of the grasping pieces 15 and 16 is formed by a rod member to be inserted through the sheath 6, a support member supporting the rod member on the most distal side within the sheath 6, and an electric motor or the like driven to move this support member, may be provided as the grasping force adjustment element 51. If this is the case, by driving the electric motor or the like in accordance with the blood pressure $\rho$, the position where the rod member is supported by the support member can be changed. In this manner, with the treatment target (blood vessel) being grasped between the grasping pieces 15 and 16, the amount of deflecting of the distal portion (one of the grasping pieces 15 and 16) of the rod member varies, and the grasping force between the grasping pieces 15 and 16 varies. In addition, the control for adjusting the grasping force as in the second embodiment may be suitably adopted, as long as the grasping force adjustment element 51 is provided for varying the grasping force acting on the treatment target (blood vessel) between the grasping pieces 15 and 16.

In another embodiment, an operation button or the like may be provided as a driving operation input section to output the driving electric power from the driving electric power output source 52. In this embodiment, the surgeon may decide whether or not the driving electric power should be output. In this embodiment, the above-described notification section may be provided, for example, in the control device 3. When it is notified or determined that the blood pressure $\rho$ is lower than the blood pressure threshold $\rho$th, the surgeon will not input any operation from the operation button (driving operation input section). For this reason, the driving electric power is not output from the driving electric power output source 52 to the grasping force adjustment element 51 (heater 55), and the volume change portion 56 does not expand. Thus, the energy treatment instrument 2 is actuated in the first mode (first actuation mode). On the other hand, when it is notified or determined that the blood pressure $\rho$ is greater than or equal to the blood pressure threshold $\rho$th, the surgeon will input an operation from the operation button 18. In response, the driving electric power is output from the driving electric power output source 52 to the grasping force adjustment element 51 (heater 55), and the volume change portion 56 expands by the heat generated by the heater 55. Thus, the energy treatment instrument 2 is actuated in the second mode (second actuation mode), and the grasping force acting on the treatment target between the grasping pieces 15 and 16 increases.

In another exemplary embodiment, any of the exemplary embodiments may be combined. If this is the case, when the blood pressure $\rho$ is lower than the blood pressure threshold $\rho$th, the processor 21 executes the output control of the electric energy from the energy output sources 32 and 47 in the first seal mode, and applies the treatment energy to the blood vessel. When the blood pressure $\rho$ is greater than or equal to the blood pressure threshold $\rho$th, the processor 21 executes the output control of the electric energy from the energy output sources 32 and 47 in the second seal mode, in which the performance of sealing the blood vessel by the treatment energy is higher than in the first seal mode, and the processor 21 applies the treatment energy to the blood vessel. That is, in this embodiment, the performance of sealing the blood vessel by the treatment energy is higher in the second mode of the energy treatment instrument 2 than in the first mode. Furthermore, in this embodiment, the processor 21 increases the grasping force acting on the treatment target between the grasping pieces 15 and 16 when the blood pressure ρ is greater than or equal to the blood pressure threshold ρth (in the second mode of the energy treatment instrument 2), in comparison to when the blood pressure ρ is lower than the blood pressure threshold ρth (in the first mode of the energy treatment instrument 2).

In the above-described embodiments, an energy treatment instrument (2) of a treatment system (1) includes a first grasping piece (15), and a second grasping piece (16) configured to open and close relative to the first grasping piece (15) and configured to grasp a blood vessel between the first grasping piece (15) and the second grasping piece (16). The actuation state of the energy treatment instrument (2) is switched between a first mode for coagulating a blood vessel and a second mode for coagulating the treatment target that is different from the first mode, in accordance with the blood pressure of the blood vessel. In the treatment system (1), an energy output source (32 or 47, or both 32 and 47) is configured to output the electric energy that is to be supplied to the energy treatment instrument (2), and is configured to apply the treatment energy to the blood vessel grasped between the first grasping piece (15) and the second grasping piece (16) when the electric energy is supplied to the energy treatment instrument (2). The measurement section (41) measures the blood pressure (ρ) of a site related to the grasped blood vessel. The processor (21) is configured to execute at least one of controlling an output of the electric energy from the energy output source (32 or 47, or both 32 and 47), based on the measurement result obtained by the measurement section (41), and increasing the grasping force for grasping the blood vessel between the first grasping piece (15) and the second grasping piece (16) when the measured blood pressure (ρ) is greater than or equal to the blood pressure threshold (ρth), in comparison to when the blood pressure (ρ) is lower than the blood pressure threshold (ρth).

Another exemplary embodiment is discussed below.

A treatment method comprising:
closing a first grasping piece and a second grasping piece with respect to each other, and grasping a blood vessel between the first grasping piece and the second grasping piece;
measuring a blood pressure at a site related to the blood vessel between the first grasping piece and the second grasping piece;
supplying electric energy from an energy output source to a treatment instrument, and applying treatment energy to the blood vessel grasped between the first grasping piece and the second grasping piece, and
performing at least one of controlling output of the electric energy from the energy output source, based on the measured blood pressure, and increasing a grasping force of grasping the blood vessel between the first grasping piece and the second grasping piece when the measured blood pressure is greater than or equal to a blood pressure threshold in comparison to when the blood pressure is lower than the blood pressure threshold.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A treatment system comprising:
an energy treatment instrument including a first grasping piece, and a second grasping piece configured to grasp a blood vessel between the first grasping piece and the second grasping piece;
an energy output source configured to:
output electrical energy to be supplied to the energy treatment instrument, and
supply the electrical energy to the energy treatment instrument so that a treatment energy is applied to the grasped blood vessel grasped between the first grasping piece and the second grasping piece;
the second grasping piece including a measurement detector configured to directly contact the grasped blood vessel and measure a blood pressure at a site located on the grasped blood vessel;
a storage medium configured to store a blood pressure threshold for comparison with the measured blood pressure; and
a processor configured to:
control output of the electrical energy from the energy output source, based on a measurement result obtained by the measurement detector, and
switch an actuation state of the energy treatment instrument between a first mode for coagulating the blood vessel and a second mode for coagulating the blood vessel in accordance with a result of the comparison of the measured blood pressure and the blood pressure threshold, the second mode being different from the first mode.

2. The treatment system according to claim 1, wherein the processor is configured to:
switch to the first mode when the measured blood pressure is lower than the blood pressure threshold; and
switch to the second mode when the measured blood pressure is higher than the blood pressure threshold.

3. The treatment system according to claim 2, wherein, in the second mode, when the blood pressure is greater than or equal to the blood pressure threshold, the processor is configured to:
control the output of the electrical energy at a first period;
stop the output of the electrical energy at a second period after the first period,
determine a number of times the electrical energy was output
when the number of times the electrical energy was output is below a reference number, count a time elapsed between the first period and the second period;
when the time elapsed is equal to or greater than a reference time, resume the output of the electrical energy at a third period after the second period, such that the electrical energy is output intermittently for a plurality of times.

4. The treatment system according to claim 1, wherein the processor is configured to:
obtain an impedance between the first grasping piece and the second grasping piece;
in the first mode, stop the output of the electrical energy in response to the impedance reaching or exceeding a first impedance threshold;
in the second mode, stop the output of the electrical energy in response to the impedance reaching or exceeding a second impedance threshold that is larger than the first impedance threshold.

5. The treatment system according to claim 2, wherein in the second mode, the processor is configured to continue to stop the output of the electrical energy when the blood pressure is greater than or equal to the blood pressure threshold.

6. The treatment system according to claim 1, wherein the measurement detector is configured to measure the blood pressure at the grasped blood vessel or another blood vessel related to the grasped blood vessel.

7. The treatment system according to claim 1, wherein the first grasping piece includes a first electrode, the second grasping piece includes a second electrode, and the energy output source is configured to:
supply the output of electrical energy to the first electrode and the second electrode, and
pass a high-frequency current as the treatment energy through the blood vessel between the first grasping piece and the second grasping piece.

8. The treatment system according to claim 1, wherein the processor is configured to control the first grasping piece and the second grasping piece to grasp the blood vessel at a first grasping force in the first mode, and
control the first grasping piece and the second grasping piece to grasp the blood vessel at a second grasping force in the second mode.

9. The treatment system according to claim 8, wherein the second grasping force used in the second mode is larger than the first grasping force used in the first mode so that even when a blood vessel having a high blood pressure is to be sealed, the blood vessel can be adequately sealed using the treatment energy.

10. The treatment system according to claim 1, wherein the measurement detector comprises measurement forceps that are provided with a pair of grasping pieces and a damper, the measurement forceps being configured to grasp an artery between the grasping and measure the blood pressure at a site located on the artery.

11. The treatment system according to claim 1, wherein the processor is configured to:
switch between the first mode and the second mode,
in the first mode, output a first electric power and grasp the blood vessel with a first grasping force, and in the second mode, output a second electric power different from the first electric power and grasp the blood vessel with a second grasping force different from the first grasping force.

12. The treatment system according to claim 1, wherein the measurement detector configured to measure the blood pressure by using oscillometric method or tonometry.

13. The treatment system according to claim 2, wherein:
in the first mode, the processor is configured to control output of a first total amount of treatment energy,
in the second mode, the processor is configured to control output of a second total amount of treatment energy, and
the first total amount of treatment energy is smaller than the second total amount of treatment energy.

14. The treatment system according to claim 13, wherein:
in the first mode, the processor is configured to control output of the electrical energy during a first period,
in the second mode, the processor is configured to control output of the electrical energy during a second period, the first period is shorter than the second period.

15. The treatment system according to claim 2, wherein: the processor is configured to:
in the first mode, output of the electrical energy in a first output period at a first output; and
in the second mode, output of the electrical energy in a second output period at a second output; and
the first output period is shorter than the second output period.

16. The treatment system according to claim 2, wherein: the processor is configured to
in a first mode, obtain a first rate of increase of impedance, and
in a second mode, obtain a second rate of increase of impedance, and
the first rate of increase of impedance is larger than the second rate of increase of impedance.

17. The treatment system according to claim 3, wherein the first period is greater than the third period, and the third period is greater than the second period.

18. A control device used with an energy treatment instrument, the energy treatment instrument including a first grasping piece, a second grasping piece configured to open and close with respect to the first grasping piece so as to grasp a blood vessel between the first grasping piece and the second grasping piece, the second grasping piece including a blood pressure sensor configured to directly contact the blood vessel, the control device comprising:
an energy output source configured to:
supply electrical energy to the energy treatment instrument configured to apply a treatment energy to the blood vessel grasped between a first grasping piece and a second grasping piece of the energy treatment instrument; and
a processor configured to:
obtain a blood pressure, from the blood pressure sensor, at a site located on the grasped blood vessel;
control output of the electrical energy from the energy output source based on a comparison result of the obtained blood pressure with a blood pressure threshold stored or set in advance; and
increase a grasping force on the blood vessel between the first grasping piece and the second grasping piece when the obtained blood pressure is greater than or equal to the blood pressure threshold in comparison to when the blood pressure is lower than the blood pressure threshold.

19. A treatment method comprising:
grasping a treatment target between a first grasping piece and a second grasping piece by using an energy treatment instrument, the energy treatment instrument including the first grasping piece, and the second grasping piece configured to open and close with respect to the first grasping; piece, the second grasping piece including a blood pressure sensor configured to directly contact the treatment target
outputting electrical energy that is to be supplied to the energy treatment instrument so a treatment energy is applied to the treatment target grasped between the first grasping piece and the second grasping piece;
measuring a blood pressure using the blood pressure sensor at a site located on the grasped treatment target; and
controlling output of the electrical energy based on a comparison result of the measured blood pressure with a blood pressure threshold stored or set in advance, and thereby switching an actuation state of the energy treatment instrument between a first mode for coagulating the treatment target and a second mode for coagulating the treatment target, the second mode being different from the first mode.

20. The treatment method of claim 19, wherein:
in the first mode, the treatment target to be coagulated with the treatment energy is grasped with a first grasping force; and
in the second mode, the treatment target to be coagulated with the treatment energy is grasped with a second grasping force that is different from the first grasping force.

21. The treatment method according to claim 20, wherein the second grasping force used in the second mode is larger than the first grasping force used in the first mode so that even when a blood vessel having a high blood pressure is to be sealed, the blood vessel can be adequately sealed using the treatment energy.

\* \* \* \* \*